United States Patent
Tada et al.

(10) Patent No.: US 11,088,334 B2
(45) Date of Patent: Aug. 10, 2021

(54) ORGANIC ELECTROLUMINESCENT ELEMENT

(71) Applicant: NIPPON STEEL & SUMIKIN CHEMICAL CO., LTD., Tokyo (JP)

(72) Inventors: Masashi Tada, Tokyo (JP); Yuichi Sawada, Tokyo (JP); Katsuhide Noguchi, Tokyo (JP)

(73) Assignee: NIPPON STEEL CHEMICAL & MATERIAL CO., LTD., Tokyo (JP)

( * ) Notice: Subject to any disclaimer, the term of this patent is extended or adjusted under 35 U.S.C. 154(b) by 344 days.

(21) Appl. No.: 16/078,231

(22) PCT Filed: Feb. 10, 2017

(86) PCT No.: PCT/JP2017/004980
§ 371 (c)(1),
(2) Date: Aug. 21, 2018

(87) PCT Pub. No.: WO2017/159152
PCT Pub. Date: Sep. 21, 2017

(65) Prior Publication Data
US 2019/0103562 A1 Apr. 4, 2019

(30) Foreign Application Priority Data
Mar. 15, 2016 (JP) .............................. JP2016-050402

(51) Int. Cl.
*H01L 51/50* (2006.01)
*H01L 51/00* (2006.01)
(Continued)

(52) U.S. Cl.
CPC .......... *H01L 51/0072* (2013.01); *C09K 11/06* (2013.01); *H01L 51/0067* (2013.01);
(Continued)

(58) Field of Classification Search
None
See application file for complete search history.

(56) References Cited

U.S. PATENT DOCUMENTS

2010/0187977 A1 7/2010 Kai et al.
2010/0295444 A1 11/2010 Kuma et al.
(Continued)

FOREIGN PATENT DOCUMENTS

JP 2012-528088 A 11/2012
JP 2012-531383 A 12/2012
(Continued)

OTHER PUBLICATIONS

English translation of International Preliminary Report on Patentability and Written Opinion dated Sep. 27, 2018, in PCT/JP2017/004980 (Forms PCT/IB/338, PCT/IB/373, and PCT/ISA/237).
(Continued)

*Primary Examiner* — Gregory D Clark
(74) *Attorney, Agent, or Firm* — Birch, Stewart, Kolasch & Birch, LLP

(57) ABSTRACT

Provided is an organic electroluminescence device (organic EL device) that is driven at a low voltage, exhibits high luminous efficiency and has a long service life. The organic EL device contains one or more light emitting layers and one or more electron transport layers between opposing anode and cathode, wherein at least one of the electron transport
(Continued)

layers contains a an indolocarbazole compound represented by general formula (1) below and an electron donor. In the formula, ring A represents an aromatic hydrocarbon ring represented by formula (1a), ring B represents a heterocyclic ring represented by formula (1b), L represents a single bond or aromatic hydrocarbon group, X represents N or C—$Ar^1$ and at least one of X represents N, and Y and $Ar^1$ represent a hydrogen atom, aromatic hydrocarbon group or aromatic heterocyclic group.

8 Claims, 1 Drawing Sheet

(51) Int. Cl.
  *C09K 11/06* (2006.01)
  *C07D 487/04* (2006.01)
(52) U.S. Cl.
  CPC .......... *H01L 51/0071* (2013.01); *H01L 51/50* (2013.01); *H01L 51/5012* (2013.01); *C07D 487/04* (2013.01); *H01L 51/0073* (2013.01); *H01L 51/0074* (2013.01); *H01L 51/0085* (2013.01); *H01L 51/508* (2013.01); *H01L 51/5076* (2013.01); *H01L 2251/308* (2013.01); *H01L 2251/5384* (2013.01)

(56) References Cited

U.S. PATENT DOCUMENTS

| | | | |
|---|---|---|---|
| 2011/0037062 A1* | 2/2011 | Fukumatsu | C07D 471/04 257/40 |
| 2012/0068170 A1 | 3/2012 | Pflumm et al. | |
| 2012/0097899 A1 | 4/2012 | Parham et al. | |
| 2012/0241732 A1 | 9/2012 | Endo et al. | |
| 2012/0305903 A1 | 12/2012 | Kai et al. | |

FOREIGN PATENT DOCUMENTS

| | | |
|---|---|---|
| WO | WO 2008/056746 A1 | 5/2008 |
| WO | WO 2009/116377 A1 | 9/2009 |
| WO | WO 2010/134350 A1 | 11/2010 |
| WO | WO 2011/070963 A1 | 6/2011 |
| WO | WO 2011/099374 A1 | 8/2011 |
| WO | WO 2013/175746 A1 | 11/2013 |
| WO | WO 2013/175747 A1 | 11/2013 |
| WO | WO 2017/025164 A1 | 2/2017 |

OTHER PUBLICATIONS

International Search Report (PCT/ISA/210) issued in PCT/JP2017/004980, dated Apr. 25, 2017.
Written Opinion (PCT/ISA/237) issued in PCT/JP2017/004980, dated Apr. 25, 2017.

* cited by examiner

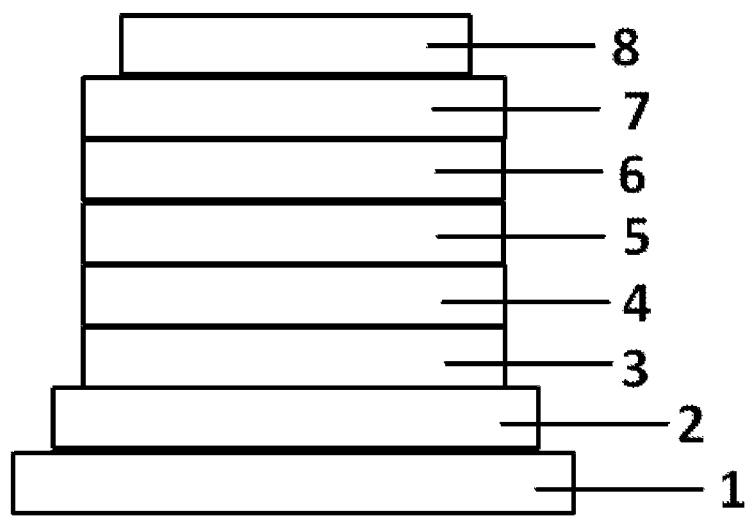

ORGANIC ELECTROLUMINESCENT ELEMENT

TECHNICAL FIELD

The present invention relates to an organic electroluminescent device or element (or hereinafter referred to as an "organic EL device").

BACKGROUND ART

When a voltage is applied to an organic EL device, holes are injected from the anode to a light emitting layer while electrons are injected from the cathode to the light emitting layer. In the light emitting layer, the injected holes and electrons are recombined resulting in the formation of excitons. At this time, singlet excitons and triplet excitons are formed at a ratio of 1:3 in accordance with the statistics of electron spin. Organic EL devices of the fluorescence emission type that utilize emission of light by singlet excitons are said to have a limit of internal quantum efficiency of 25%. On the other hand, organic EL devices of the phosphorescence emission type that utilize emission of light by triplet excitons are said to enhance internal quantum efficiency up to 100% in the case of having efficiently carried out intersystem crossing from singlet excitons.

However, phosphorescence emission type organic EL devices encounter technical problems when attempting to lengthen service life.

More recently, highly efficient organic EL devices have been developed that utilize delayed fluorescence. For example, PTL 1 discloses an organic EL device that utilizes one of the mechanisms of delayed fluorescence in the form of triplet-triplet fusion (TTF). This TTF mechanism utilizes the phenomenon by which a singlet exciton is formed by the collision of two triplet excitons, and is thought to theoretically enhance internal quantum efficiency by up to 40%. However, since efficiency is still lower when compared with organic EL devices of the phosphorescence emission type, further improvement of efficiency is required.

PTL 2 discloses an organic EL device that utilizes a thermally activated delayed fluorescence (TADF) mechanism. The TADF mechanism utilizes the phenomenon by which intersystem crossing occurs from triplet excitons to singlet excitons in materials having a small energy difference between the singlet level and triplet level, and is thought to theoretically enhance internal quantum efficiency by up to 100%. However, further improvement of service life characteristics in the same manner as devices of the phosphorescence emission type.

CITATION LIST

Patent Literature

[PTL 1] WO 2010/134350
[PTL 2] WO 2011/070963
[PTL 3] WO 2009/0116377
[PTL 4] WO 2011/0099374
[PTL 5] WO 2013/0175746
[PTL 6] WO 2013/0175747

PTL 3 discloses the use of an indolocarbazole compound in an electron transport layer. PTL 4 discloses the use of an indolocarbazole compound in an electron transport layer and hole blocking layer. PTL 5 and 6 each disclose the use of an azine compound in an electron transport layer.

However, none of these can be said to be adequate and further improvement is desired.

SUMMARY OF INVENTION

In order to apply organic EL devices to such applications as the display elements of flat panel displays or light sources, it is necessary to improve the luminous efficiency of the device while at the same time ensuring adequate stability when driven. With the foregoing in view, an object of the present invention is to provide an organic EL device that is useful in terms of practical use by having high efficiency and high stability when driving despite being driven at a low voltage.

The present invention is an organic EL device containing one or more light emitting layers and one or more electron transport layers between opposing anode and cathode, wherein at least one of the electron transport layers contains a compound represented by general formula (1) below and an electron donor.

[C1]

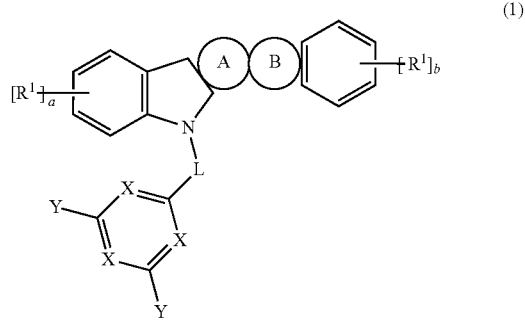

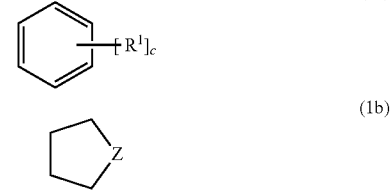

Here, ring A represents an aromatic hydrocarbon ring represented by formula (1a), ring B represents a heterocyclic ring represented by formula (1b), and ring A and ring B are condensed with a ring adjacent to ring A and ring B at arbitrary locations, L represents a single bond, or aromatic hydrocarbon group having 6 to 12 carbon atoms, X represents N or C—$Ar^1$ and at least one of X represents N, Y and $Ar^1$ respectively and independently represent a hydrogen atom, substituted or unsubstituted aromatic hydrocarbon group having 6 to 18 carbon atoms, substituted or unsubstituted aromatic heterocyclic group having 3 to 18 carbon atoms, or a linked aromatic group obtained by linking 2 to 5 of these aromatic rings, $R^1$ independently represents an aliphatic hydrocarbon group having 1 to 10 carbon atoms, a substituted or unsubstituted aromatic hydrocarbon group having 6 to 10 carbon atoms, or a substituted or unsubstituted aromatic heterocyclic group having 3 to 12 carbon atoms, and a, b and c respectively and independently represent an integer of 0 to 3, Z represents N—Ar², C(R²)₂, O or S, Ar² represents a substituted or unsubstituted aromatic hydrocarbon group having 6 to 18 carbon atoms, a substituted or unsubstituted aromatic heterocyclic group having 3 to 18 carbon atoms, or a linked aromatic group obtained by linking 2 to 5 of these aromatic rings, and R² independently represents a hydrogen atom, aliphatic hydrocarbon group having 1 to 10 carbon atoms, substituted or unsubstituted aromatic hydrocarbon group having 6 to 10 carbon atoms, or substituted or unsubstituted aromatic heterocyclic group having 3 to 12 carbon atoms.

A preferable aspect of formula (1b) is formula (1d), and a preferable aspect of L is a single bond:

[C2]

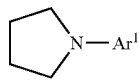

(1d)

where, Ar¹ has the same meaning as in general formula (1).

The electron transport layer is formed of two layers including a first electron transport layer being adjacent to the light emitting layer and a second electron transport layer being adjacent to the first layer, and first electron transport layer contains a compound represented by general formula (1), and the second transport layer contains a compound represented by general formula (1) and an electron donor.

The above-mentioned electron donor is preferably an alkaline metal compound or alkaline metal complex and more preferably quinolilato-lithium (Liq).

The electron transport layer is obtained by depositing a premix of a compound represented by general formula (1) and electron donor, and the light emitting layer contains a host material and a luminescent material, and preferably the host material contains a compound represented by general formula (1).

As a result of containing a specific electron transport material and electron donor in the electron transport layer, the organic EL device of the present invention can be an organic EL device having high luminous efficiency and long service life that is driven at a low voltage.

BRIEF DESCRIPTION OF DRAWINGS

FIG. 1 is a schematic cross-sectional diagram showing one example of an organic EL device.

DESCRIPTION OF EMBODIMENTS

The organic EL device of the present invention contains one or more light emitting layers and one or more electron transport layers between opposing anode and cathode, wherein at least one electron transport layer contains a compound represented by the above-mentioned general formula (1) and an electron donor.

The following provides an explanation of general formula (1).

Ring A represents an aromatic hydrocarbon ring represented by formula (1a). In addition, ring B represents a heterocyclic ring represented by formula (1b), and ring A and ring B are each bonded to an adjacent ring at an arbitrary location.

L represents a single bond or divalent aromatic hydrocarbon group having 6 to 12 carbon atoms. L preferably represents a single bond or phenylene group, and more preferably a single bond.

Specific examples of the above-mentioned aromatic hydrocarbon group having 6 to 12 carbon atoms include a phenylene group, biphenylene group and naphthalene group.

X represents N or C—Ar¹ and at least one of X represents N.

Y and Ar¹ respectively and independently represent a hydrogen atom, substituted or unsubstituted aromatic hydrocarbon group having 6 to 18 carbon atoms, a substituted or unsubstituted aromatic heterocyclic group having 3 to 18 carbon atoms, or a linked aromatic group obtained by linking 2 to 5 of these aromatic rings, preferably a hydrogen atom, substituted or unsubstituted aromatic hydrocarbon group having 6 to 12 carbon atoms, substituted or unsubstituted aromatic heterocyclic group having 3 to 12 carbon atoms or a linked aromatic group obtained by linking 2 to 3 of these aromatic rings, and more preferably a hydrogen atom or substituted or unsubstituted aromatic hydrocarbon group having 6 to 12 carbon atoms.

Specific examples of the above-mentioned aromatic hydrocarbon group having 6 to 18 carbon atoms, aromatic heterocyclic group having 3 to 18 carbon atoms, or linked aromatic groups thereof in the case of being unsubstituted include benzene, naphthalene, phenanthrene, anthacene, triphenylene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, thiadiazole, benzotriazine, phthalazine, tetrazole, indole, benzofuran, benzothiophene, benzoxazole, benzothiazole, benzimidazole, benzotriazole, benzoisothiazole, benzothiadiazole, dibenzofuran, dibenzothiophene, dibenzoselenophene, carbazole and aromatic groups formed from linked aromatic compounds obtained by linking 2 to 5 of these aromatic rings with single bonds. Preferable examples include benzene, naphthalene, pyridine, pyrimidine, triazine, quinoline, quinazoline and aromatic groups formed by removing a single hydrogen atom from linked aromatic compounds obtained by linking 2 to 5 thereof. More preferable examples include benzene, naphthalene and aromatic groups formed from linked aromatic compounds obtained by linking 2 to 3 thereof.

Here, a linked aromatic group as referred to in the present description refers to an aromatic group obtained by linking a plurality of aromatic hydrocarbon groups having the above-mentioned number of carbon atoms or aromatic rings possessed by aromatic heterocyclic groups by direct bonding, and the plurality of aromatic rings may be the same or different.

The linked aromatic compound may be a linear type in the manner of Ar¹¹-Ar¹²-Ar¹³ or may be a branched type in the manner of Ar¹¹-Ar¹², (Ar¹³), and Ar¹¹ to Ar¹³ may be the same or different. Furthermore, Ar¹³ is not required to be present, and Ar¹⁴ and Ar¹³ may be included. Bonds of aromatic groups formed from the linked aromatic compound may be formed from a terminal Ar¹¹ or Ar¹³ or may be formed from an intermediate Ar¹². Here, Ar¹¹ to Ar¹³ are aromatic groups or aromatic rings.

These aromatic hydrocarbon groups, aromatic heterocyclic groups or linked aromatic groups may each have a substituent. Preferable substituents in the case of having a substituent are cyano groups and aliphatic hydrocarbon groups having 1 to 10 carbon atoms. Furthermore, the number of substituents is 0 to 5 and preferably 0 to 2. The number of carbon atoms of the substituents is not included when calculating the number of carbon atoms in the case of having an aromatic hydrocarbon group, aromatic heterocyclic group or linked aromatic group. However, the total number of carbon atoms, include the number of carbon atoms of substituents, preferably satisfies the above-mentioned range.

Specific examples of the above-mentioned substituents include cyano, methyl, ethyl, propyl, butyl, pentyl, hexyl, heptyl, octyl, nonyl and decyl groups. The above-mentioned substituent is preferably a cyano group or C1-C6 alkyl group.

$R^1$ independently represents an aliphatic hydrocarbon group having 1 to 10 carbon atoms, a substituted or unsubstituted aromatic hydrocarbon group having 6 to 10 carbon atoms, or a substituted or unsubstituted aromatic heterocyclic group having 3 to 12 carbon atoms. $R^1$ preferably represents an aliphatic hydrocarbon group having 1 to 6 carbon atoms, a substituted or unsubstituted aromatic hydrocarbon group having 6 to 8 carbon atoms, or a substituted or unsubstituted aromatic heterocyclic group having 3 to 9 carbon atoms. $R^1$ more preferably represents a phenyl group.

Specific examples of the above-mentioned aliphatic hydrocarbon groups having 1 to 10 carbon atoms include methyl, ethyl, propyl, butyl, pentyl, hexyl, heptyl, octyl, nonyl and decyl groups. The aliphatic hydrocarbon group having 1 to 10 carbon atoms is preferably a C1-C6 alkyl group.

Specific examples of the above-mentioned aromatic hydrocarbon groups having 6 to 10 carbon atoms or aromatic heterocyclic groups having 3 to 12 carbon atoms in the case of being unsubstituted include aromatic groups formed by removing a single hydrogen atom from benzene, naphthalene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, benzotriazine, phthalazine, tetrazole, indole, benzofuran, benzothiophene, benzoxazole, benzothiazole, indazole, benzimidazole, benzotriazole, benzoisothiazole, benzothiadiazole, dibenzofuran, dibenzothiophene, dibenzoselenophene or carbazole. Preferable examples include aromatic groups formed by removing a single hydrogen atom from benzene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, benzotriazine, phthalazine, tetrazole, indole, benzofuran, benzothiophene, benzoxazole, benzothiazole, indazole, benzimidazole, benzotriazole, benzoisothiazole or benzothiadiazole. More preferable examples include aromatic groups formed by removing a single hydrogen atom from benzene.

The aromatic hydrocarbon groups or aromatic heterocyclic groups may each have a substituent. Preferable substituents in the case of having a substituent are the same as the substituents explained for $Ar^1$.

a, b and c respectively and independently represent an integer of 0 to 3, preferably represent an integer of 0 to 2, and more preferably represent an integer of 0 or 1.

Z represents N—$Ar^2$, $C(R^2)_2$, O or S. Z preferably represents N—$Ar^2$ and is represented by formula (1d) in this case. Here, $Ar^2$ is the same as that explained for $Ar^1$ with the exception of not representing a hydrogen atom. $R^2$ is the same as that explained for $R^1$ with the exception of including the case of representing a hydrogen atom.

Although the following indicates specific examples of compounds represented by general formula (1), compound represented by general formula (1) are not limited to these exemplified compounds.

[C3]

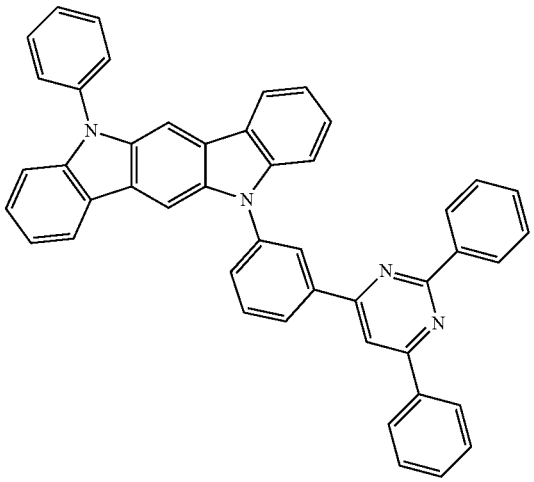

1

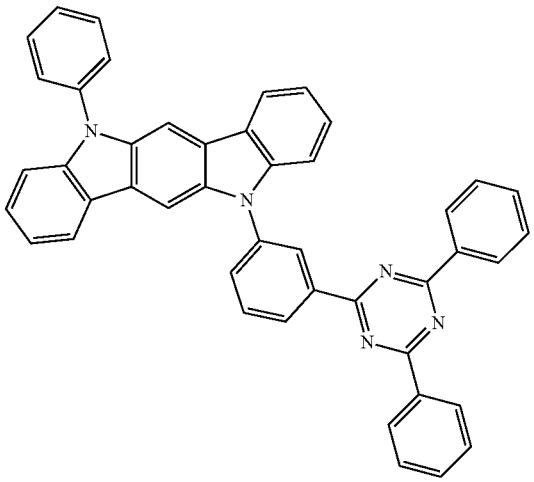

2

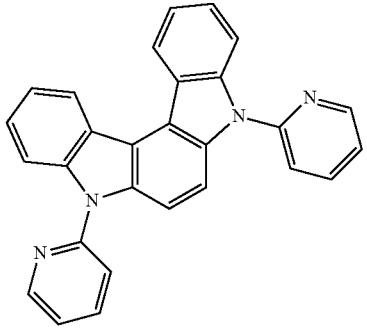

3

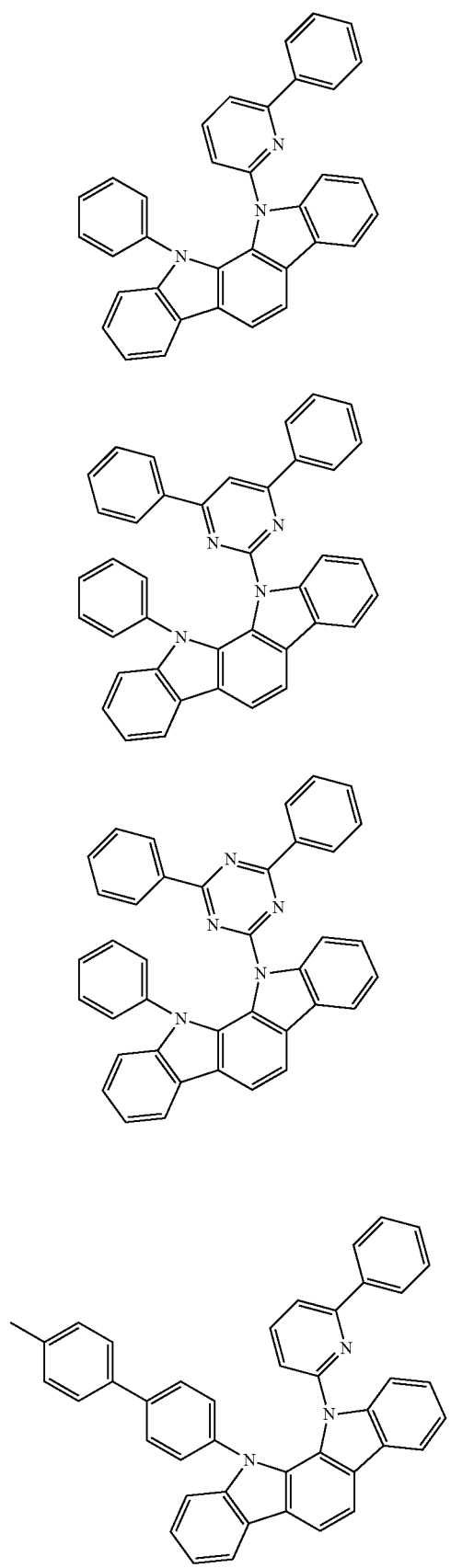
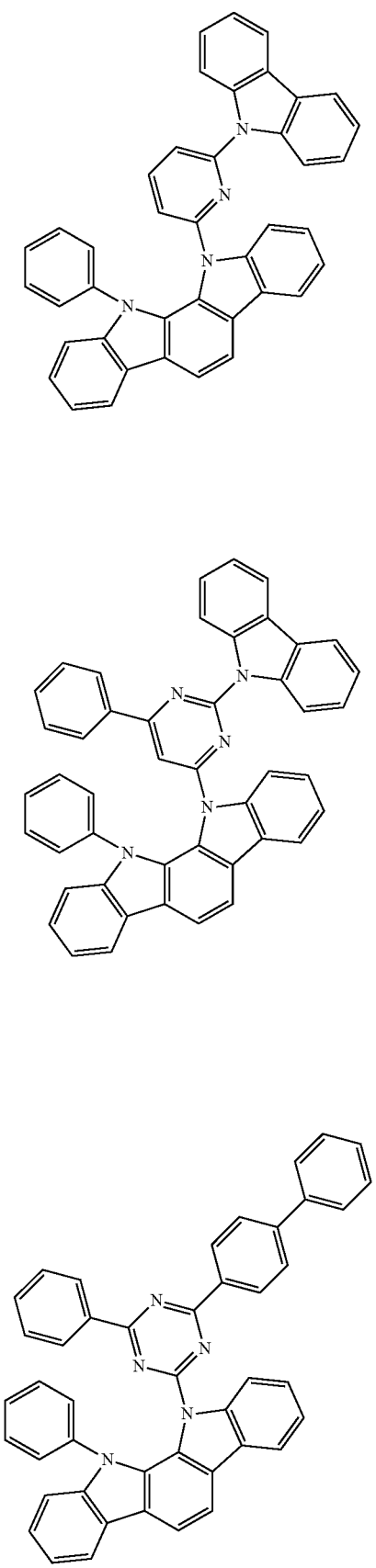

11
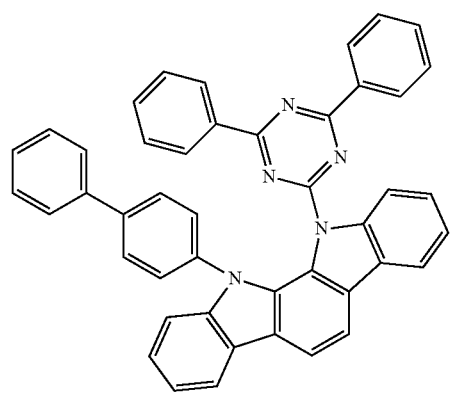
12
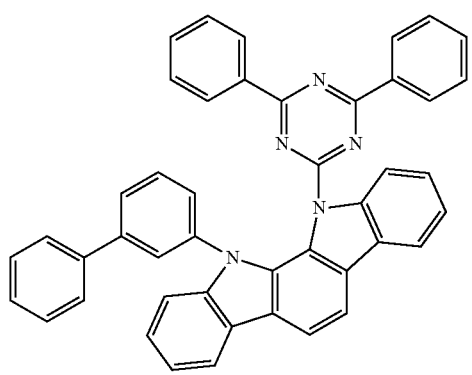
13
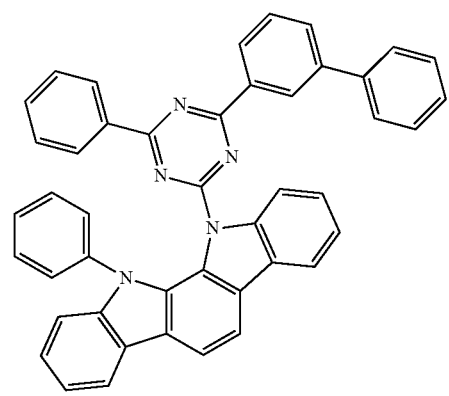
14
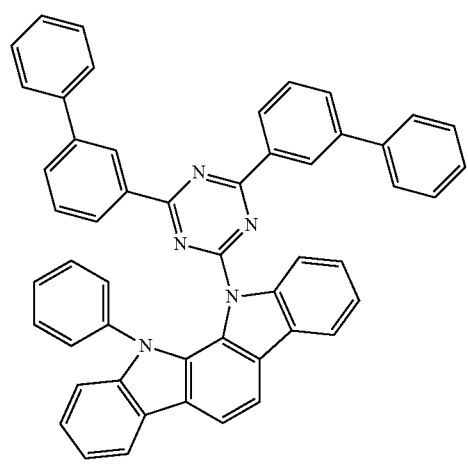
15
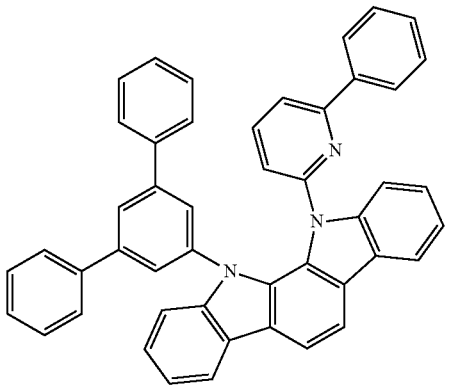
16
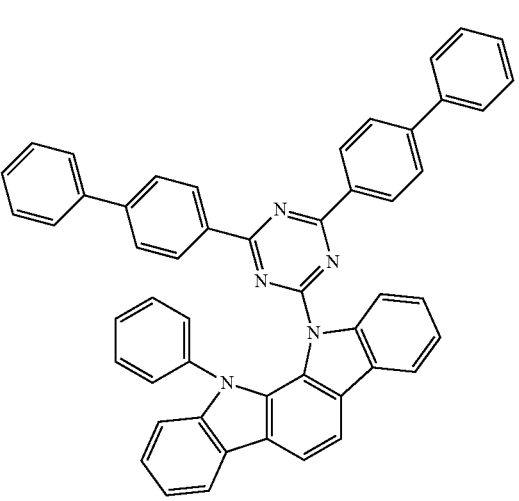
17
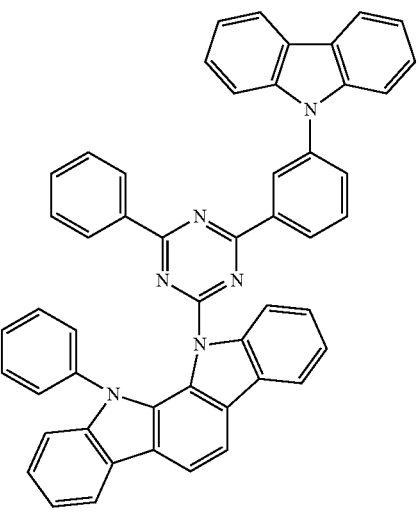

[C4]
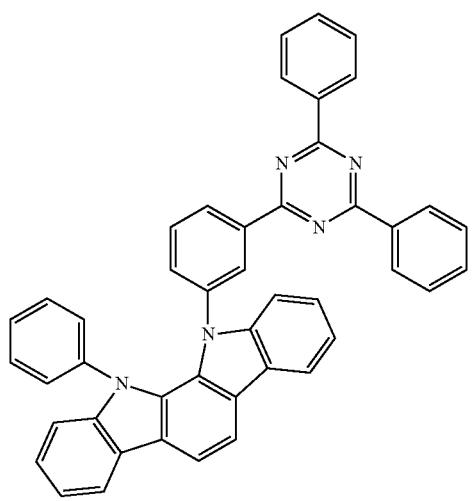
18
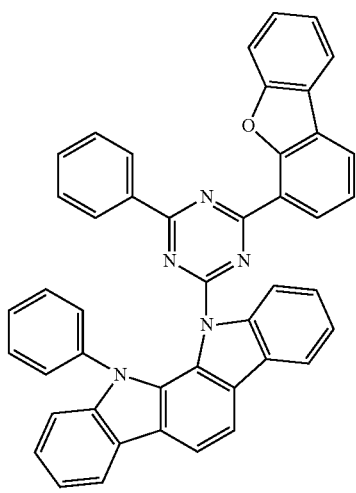
21
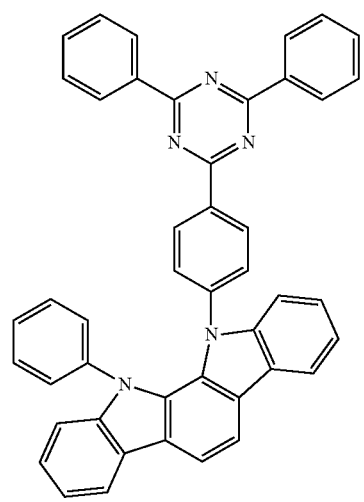
19
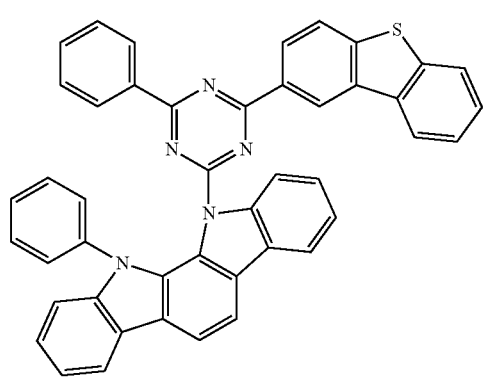
22
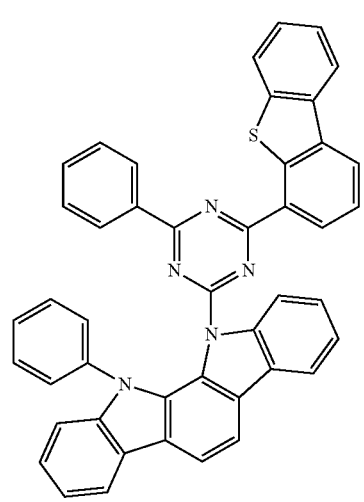
20
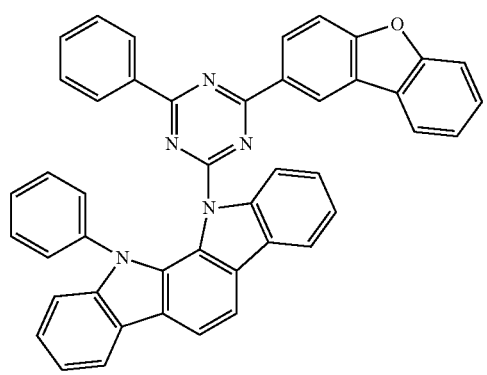
23

24
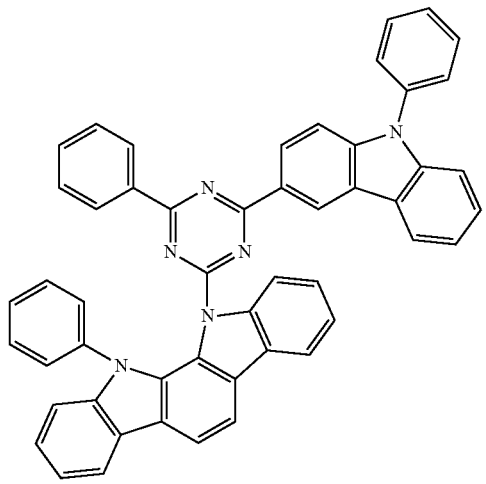
25
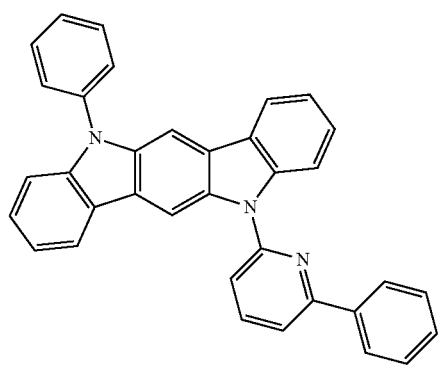
26
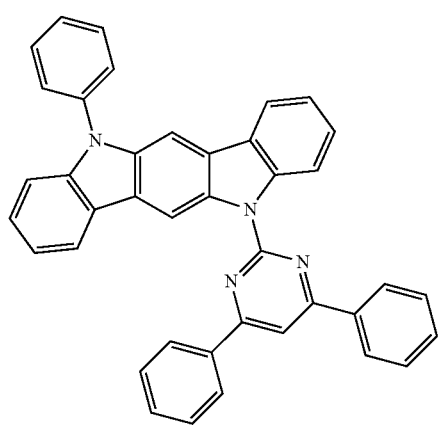
27
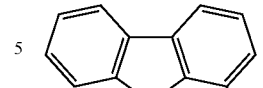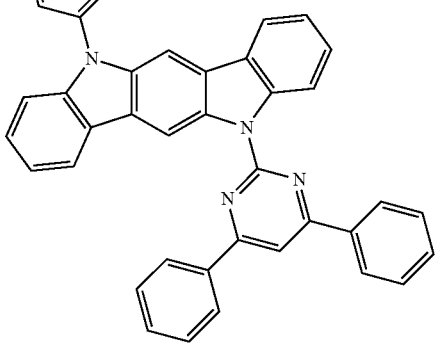
28
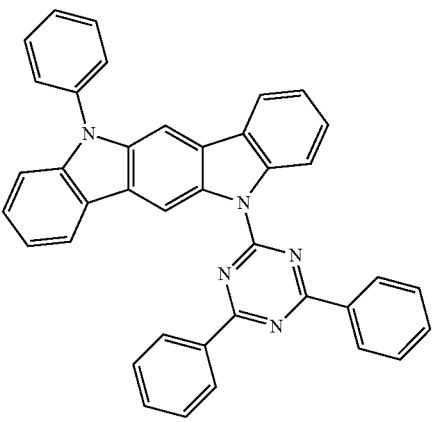
29
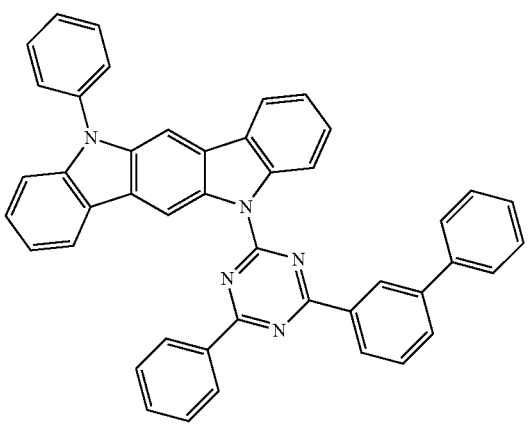

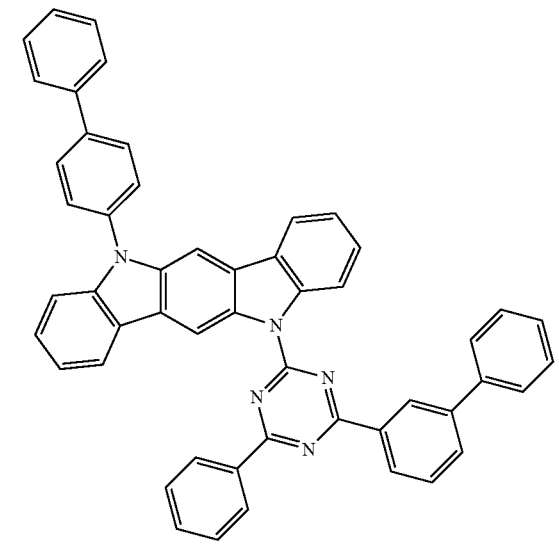
30
[C5]
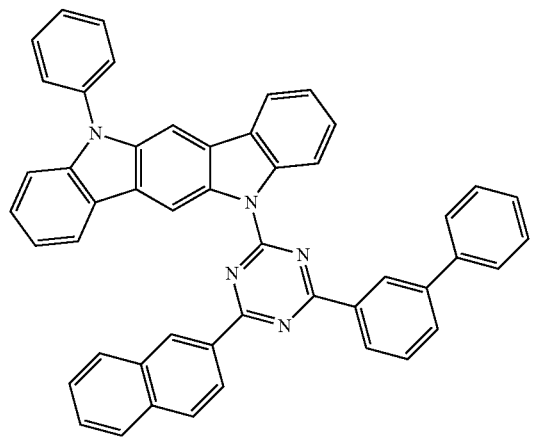
31
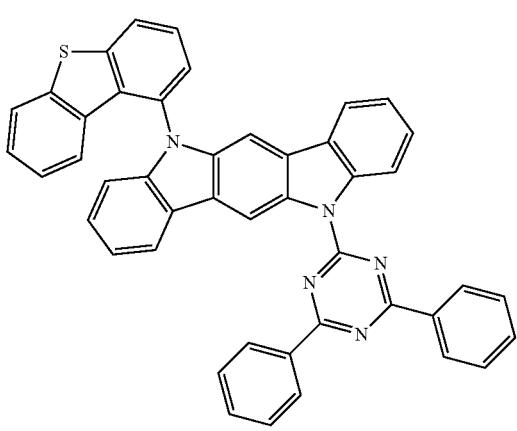
32
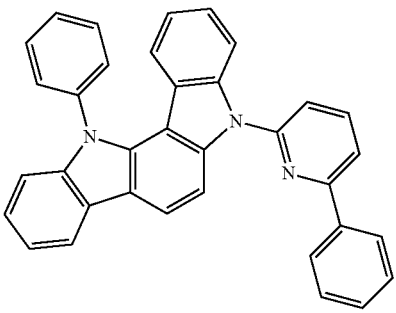
33
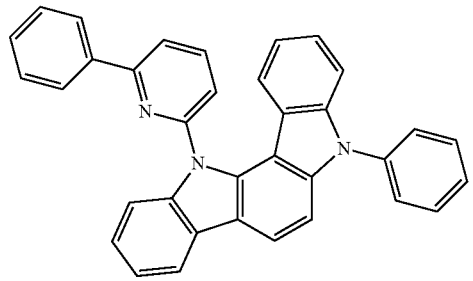
34
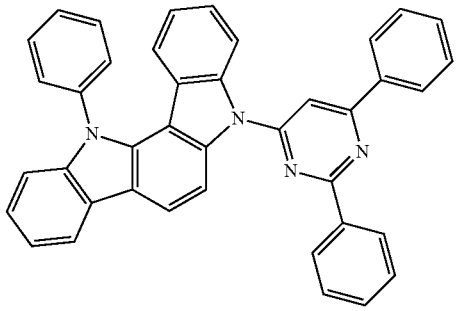
35
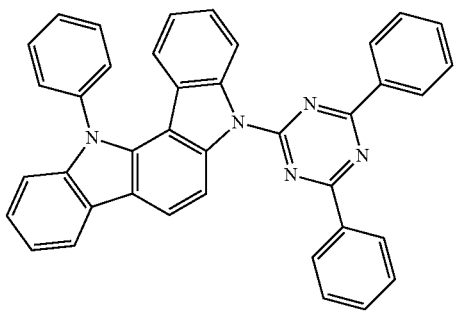
36
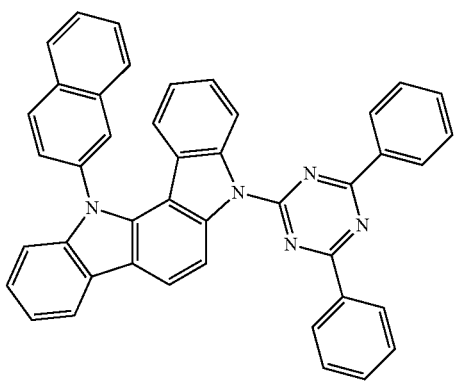
37

38
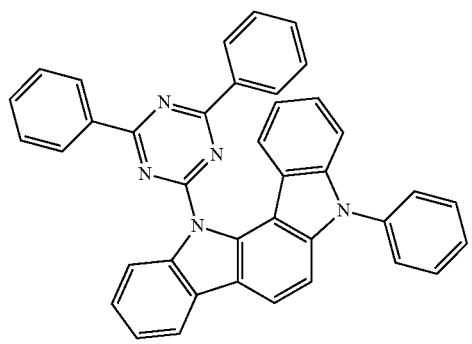
39
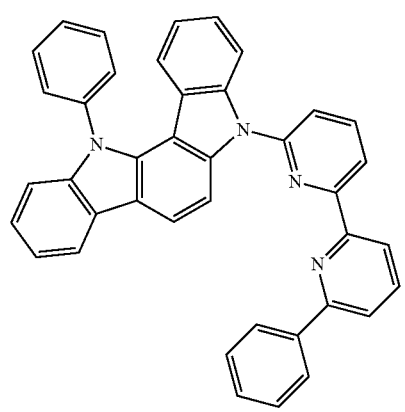
40
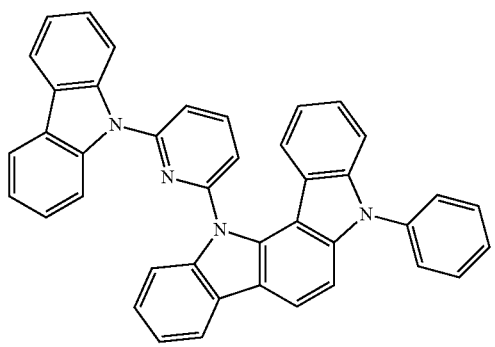
41
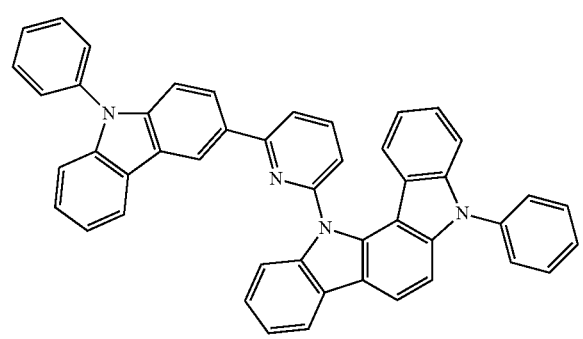
42
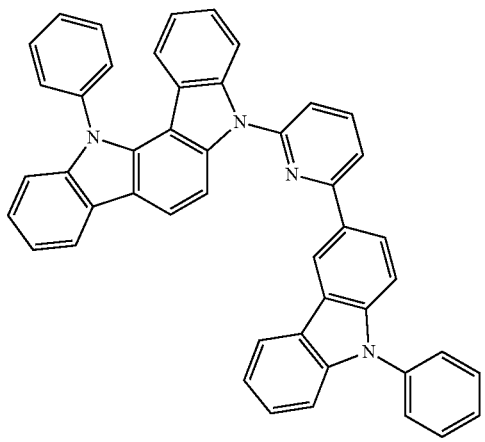
43
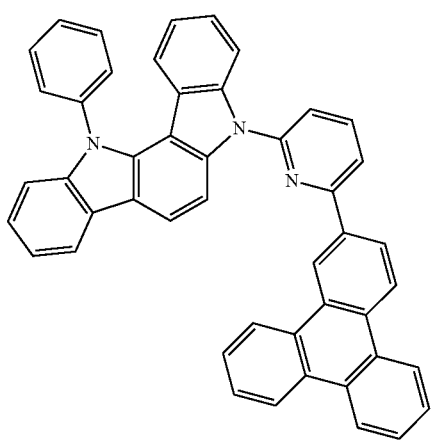
44
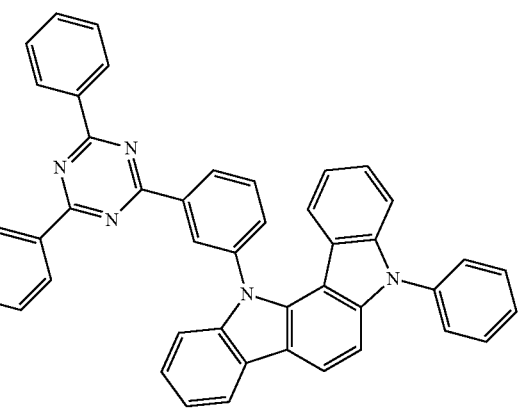
45
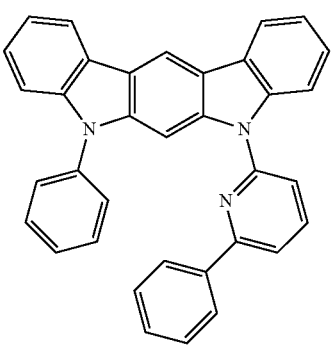

[C6]
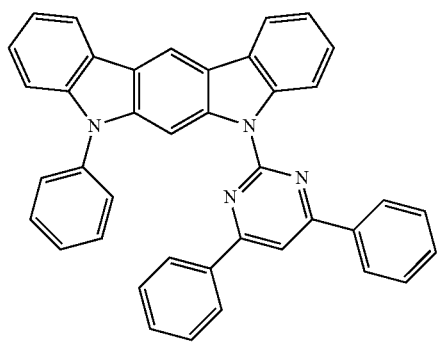
46
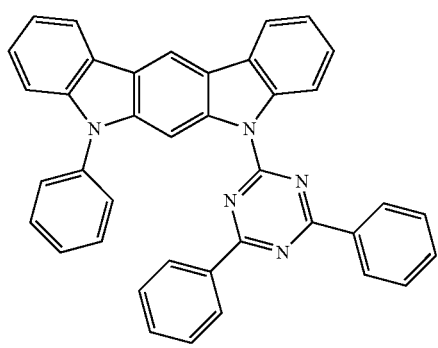
47
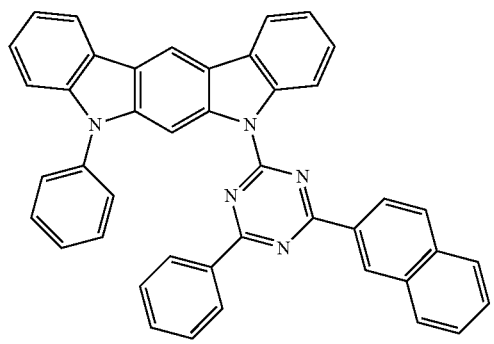
48
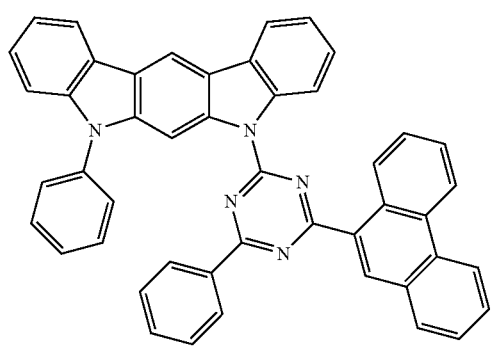
49
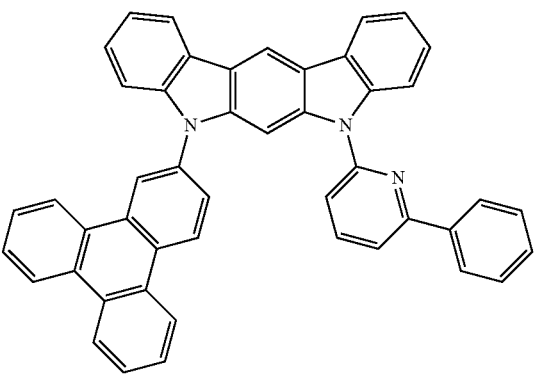
50
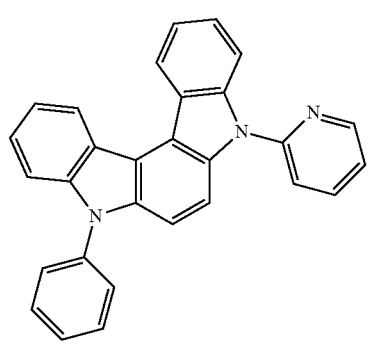
51
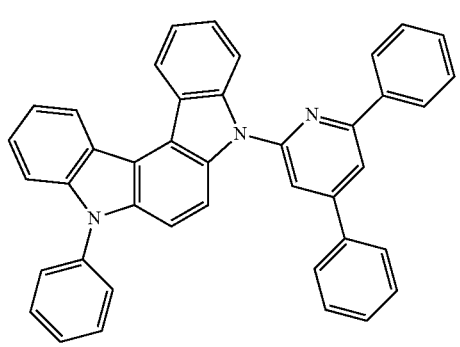
52
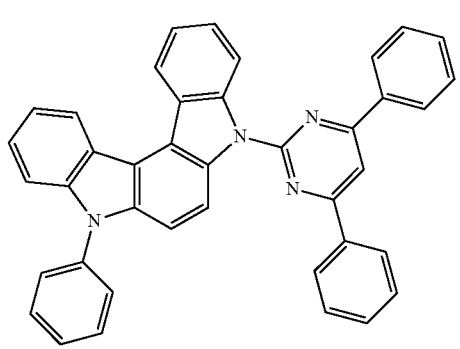
53

-continued
54
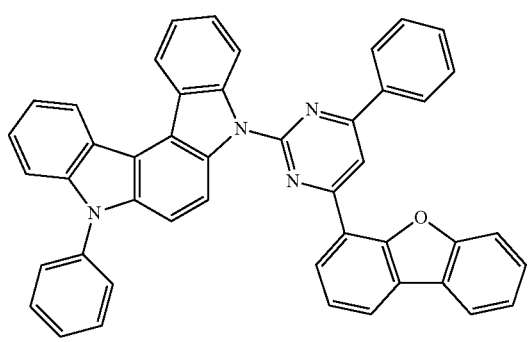
55
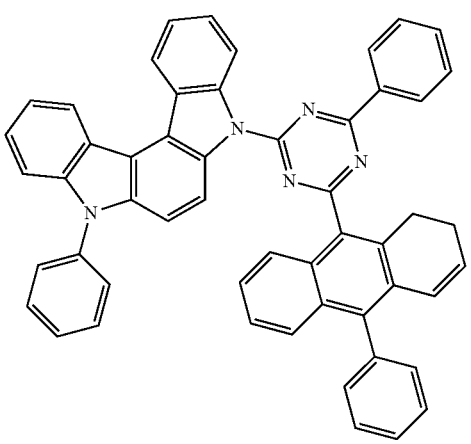
56
57
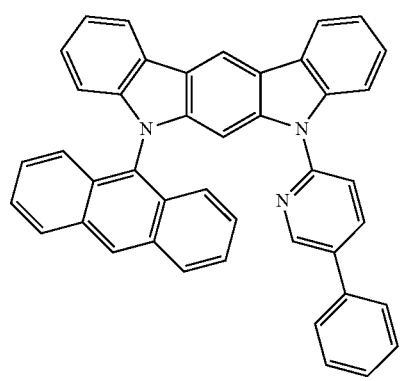
-continued
58
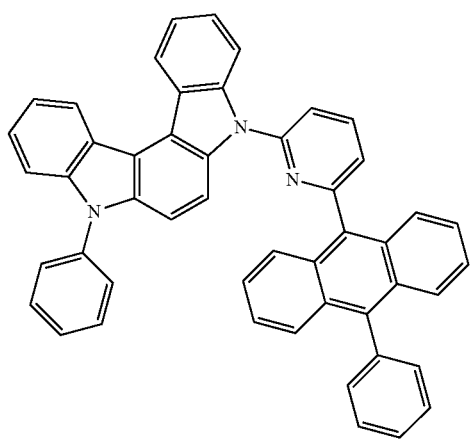
59
60
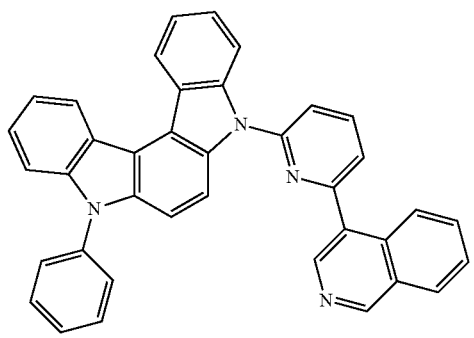
61
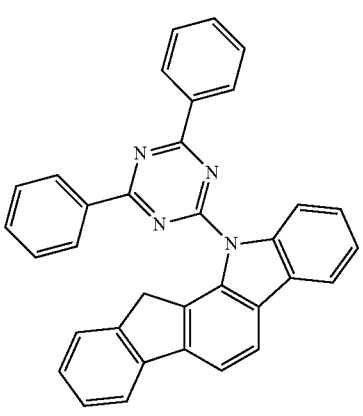

[C7]
62
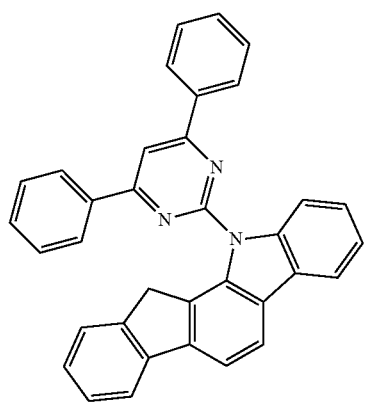
63
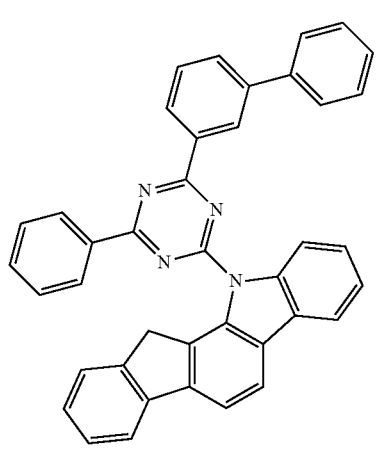
64
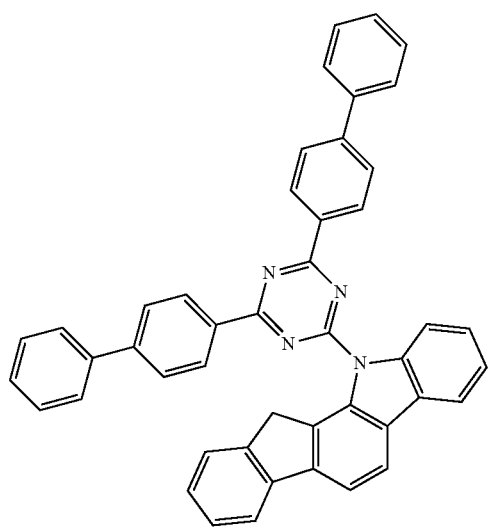
65
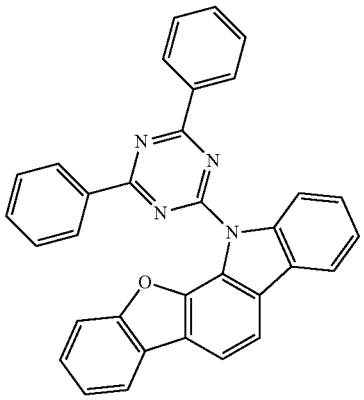
66
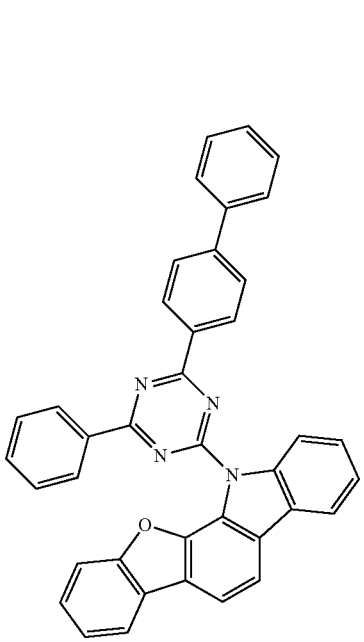
67
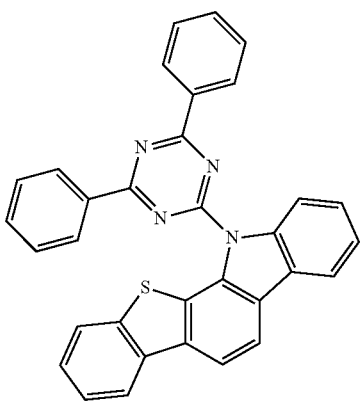

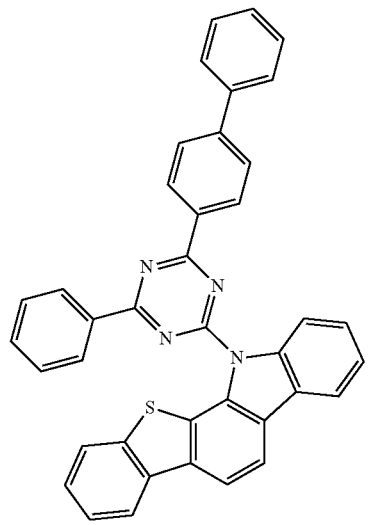
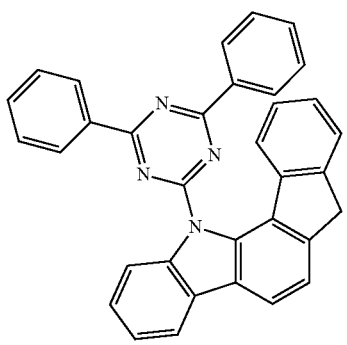
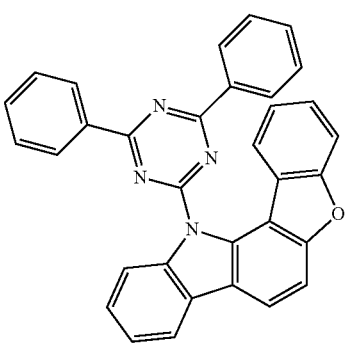
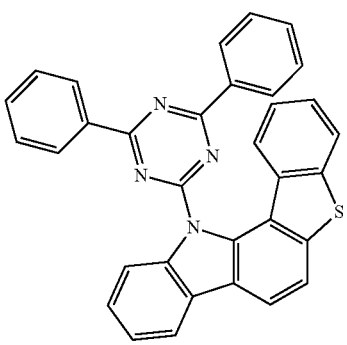
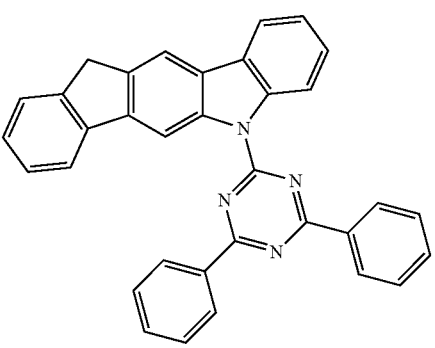

[C8]

76
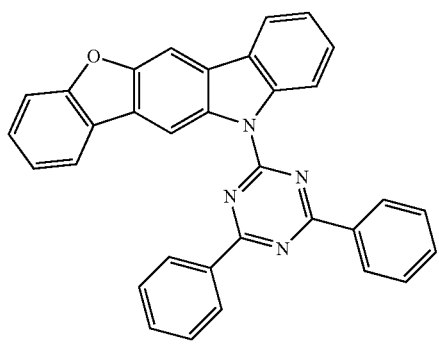

77
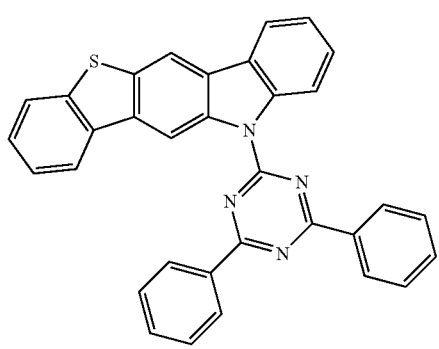

78
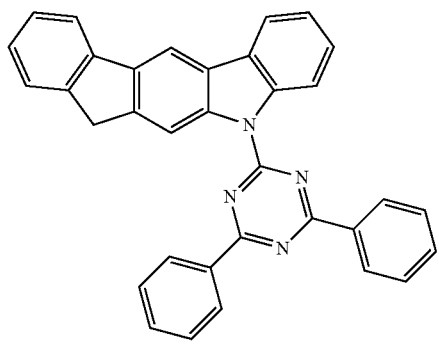

79
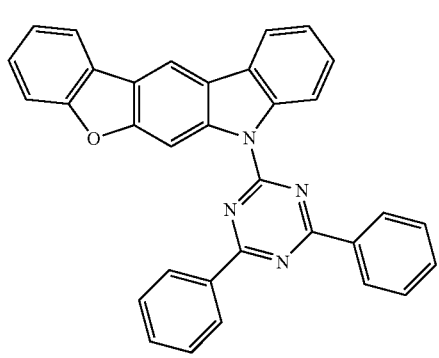

80
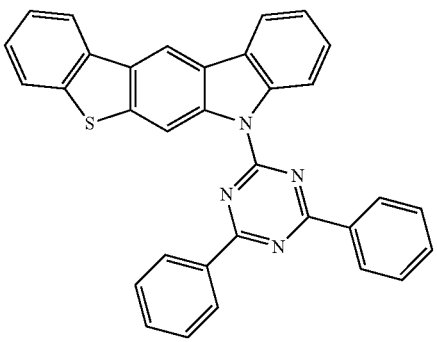

81
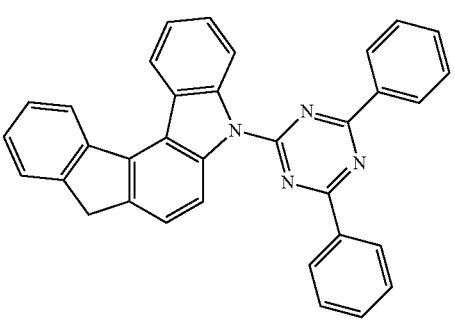

82
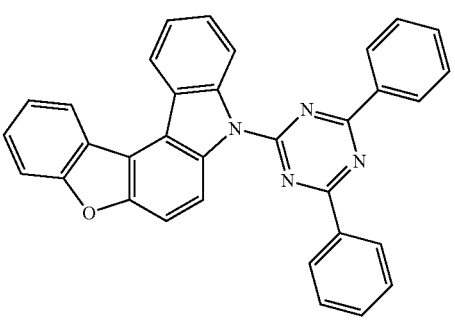

83
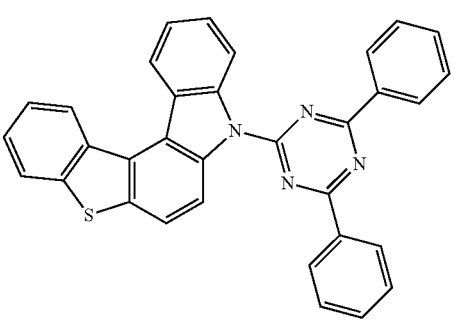

A compound, which is known to function as a compound that facilitates injection of electrons into the electron transport layer from the cathode or electron injection layer by improving the electron injection barrier, can be used for the electron donor. The electron donor is preferably a donor compound used by mixing into the electron transport material. Preferable examples of the electron donor include alkaline metals, inorganic salts containing an alkaline metal, complexes of alkaline metals and organic materials, alkaline earth metals, inorganic salts containing alkaline earth metals and complexes of alkaline earth metals and organic materials. The electron donor is preferably an inorganic salt of an alkaline metal or a complex of an alkaline metal and organic material, and more preferably Liq.

Examples of preferable types of the above-mentioned alkaline metals and alkaline earth metals include alkaline metals such as lithium, sodium, potassium, rubidium or cesium, and alkaline earth metals such as magnesium, calcium, cerium or barium, which are highly effective for improving electron transportability in terms of work function.

In addition, inorganic salts or complexes with organic materials are more preferable than metals alone due to ease of vapor deposition in air and superior handling. Moreover, complexes with organic materials are more preferable from the viewpoints of facilitating handling in air and ease of control of the added concentration thereof.

Specific examples of inorganic salts include oxides such as LiO or $Li_2O$, fluorides such as LiF, NaF or KF, and carbonates such as $Li_2CO_3$, $Na_2CO_3$, $K_2CO_3$, $Rb_2CO_3$ and $Cs_2CO_3$. In addition, preferable examples of alkaline metals or alkaline earth metals include lithium and cesium from the viewpoint of allowing obtaining a large effect of being able to be driven at a low voltage. Specific examples of organic materials in complexes with organic materials include quinolinol, benzoquinolinol, pyridyl phenol, flavonol, hydroxyimidazopyridine, hydroxybenzazole and hydroxytriazole. Among these, complexes of alkaline metals and organic materials are preferable from the viewpoint of having a greater effect in lowering the voltage of the luminescent device, and complexes of lithium and organic materials are more preferable from the viewpoints of facilitating synthesis and thermal stability, an example of which is Liq.

A superior organic EL device can be provided by using a compound represented by the above-mentioned general formula (1) and the above-mentioned electron donor as an electron transport material.

Although the electron transport layer can be used by forming only a single layer thereof, it is preferably used by forming two layers including a first electron transport layer located adjacent to the light emitting layer and a second electron transport layer located adjacent thereto. In the case of forming two electron transport layers, the first electron transport layer located adjacent to the light emitting layer preferably contains a compound represented by the above-mentioned general formula (1) while the second electron transport layer preferably contains a compound represented by the above-mentioned general formula (1) and an electron donor. In this case, the first electron transport layer can also function as a hole blocking layer.

Although a compound represented by the above-mentioned general formula (1) and an electron donor can be used by vapor-depositing from respectively different deposition sources, the above-mentioned materials are preferably premixed prior to vapor deposition to form a premix followed by simultaneously depositing that premix from a single deposition source to form an electron transport layer.

Next, although an explanation is provided of the structure of the organic EL device of the present invention with reference to the drawings, the structure of the organic EL device of the present invention is not limited thereto.

FIG. 1 is a cross-sectional view showing an example of the typical structure of an organic EL device used in the present invention, wherein reference symbol 1 represents a substrate, reference symbol 2 represents an anode, reference symbol 3 represents a hole injection layer, reference symbol 4 represents a hole transport layer, reference symbol 5 represents a light emitting layer, reference symbol 6 represents a first electron transport layer, reference symbol 7 represents a second electron transport layer and reference symbol 8 represents a cathode. The organic EL device of the present invention may also have an electron blocking layer between the light emitting layer and hole transport layer. In the organic EL device of the present invention, although the anode, light emitting layer, electron transport layers and cathode are present as essential layers, the hole injection layer and electron injection layer may also be present in addition to the essential layers, and an electron blocking layer may further be present between the hole injection/transport layer and light emitting layer. Furthermore, hole injection/transport layer refers to the hole injection layer, hole transport layer or both.

A structure opposite that of FIG. 1, namely a structure in which the layers are layered on the substrate 1 in the order of the cathode 8, second electron transport layer 7, first electron transport layer 6, light emitting layer 5, hole transport layer 4, hole injection layer 3 and anode 2, can also be employed. When implementing this, addition or omission of some of these layers is possible.

—Substrate—

The organic EL device of the present invention is preferably supported on a substrate. There are no particular limitations on this substrate and that conventionally used in organic EL devices may be used, examples of which that can be used include those formed of glass, clear plastic and quartz.

—Anode—

A material formed of a metal, alloy, electrically conductive compound or mixture thereof having a large work function (4 eV or more) is preferably used for the material of the anode in the organic EL device. Specific examples of such electrode materials include metals such as Au, and electrically conductive transparent materials such as CuI, indium tin oxide (ITO), $SnO_2$ or ZnO. In addition, amorphous materials such as IDIXO ($In_2O_3$—ZnO) that enable the production of a transparent, electrically conductive film may also be used. The anode is formed by forming these electrode materials into a thin film using a method such as vapor deposition or sputtering, and then forming a desired pattern by photolithography, or in cases in which there is no particular need for pattern accuracy (on the order of 100 μm or more), a pattern may be formed through a mask having a desired shape during vapor deposition or sputtering of the above-mentioned electrode materials. Alternatively, in the case of using a coatable substance in the manner of an organic electrically conductive compound, a wet deposition method such as a printing method or coating method can also be used. In the case of extracting light from this anode, it is preferable to make transmittance greater than 10%, and the sheet resistance of the anode is preferably several hundred Ω/□ or less. Although varying according to the material, the film thickness is normally within the range of 10 nm to 1000 nm and preferably within the range of 10 nm to 200 nm.

—Cathode—

On the other hand, a material formed of a metal (referred to as an electron injection metal), alloy, electrically conductive compound or mixture thereof having a small work function (4 eV or less) is used for the material of the cathode. Specific examples of such electrode materials include sodium, sodium-potassium alloys, magnesium, lithium, magnesium/copper mixtures, magnesium/silver mixtures, magnesium/aluminum mixtures, magnesium/indium mixtures, aluminum/aluminum oxide ($Al_2O_3$) mixtures, indium, lithium/aluminum mixtures and rare earth metals. Among these, mixtures of electron injection metals and secondary metals, which have a larger work function than these metals and are more stable, examples of which include magnesium/silver mixtures, magnesium/aluminum mixtures, magnesium/indium mixtures, aluminum/aluminum oxide ($Al_2O_3$) mixtures, lithium/aluminum mixtures and aluminum, are preferable from the viewpoints of electron injection and durability with respect to oxidation and the like. The cathode can be produced by forming these cathode materials into a thin film by a method such as vapor deposition or sputtering. In addition, sheet resistance of the cathode is preferably several hundred Ω/□ or less, and film thickness is normally selected to be within the range of 10 nm to 5 μm and preferably within the range of 50 nm to 200 nm. Furthermore, if either the anode or cathode of the organic EL device is transparent or translucent in order to allow emitted light to pass through, emission luminance improves, thereby making this preferable.

In addition, a transparent or translucent cathode can be produced by forming the above-mentioned metal on the cathode at a film thickness of 1 nm to 20 nm followed by forming an electrically conductive transparent material, as exemplified in the explanation of the anode, and applying this to produce a device in which both the anode and cathode are transparent.

—Light Emitting Layer—

The light emitting layer is a layer that emits light after having generated excitons by recombining holes and electrons injected from the anode and cathode, respectively, and the light emitting layer contains a luminescent material and preferably an organic luminescent dopant material and a host material. The light emitting layer may include a single layer or multiple layers, and the organic luminescent dopant material and host material may each include a single type or a plurality of types may be used in combination.

In the case the light emitting layer contains a luminescent material and a host material, a compound represented by the above-mentioned general formula (1) is more preferably used for the host material.

In the case a phosphorescent dopant is used for the luminescent dopant material, an organic metal complex is contained for the phosphorescent dopant that contains at least one metal selected from ruthenium, rhodium, palladium, silver, rhenium, osmium, iridium, platinum and gold. More specifically, although an iridium complex described in the J. Am. Chem. Soc., 2001, 123, 4304 and Japanese Translation of PCT Application No. 2013-53051 is used preferably, the organic metal complex is not limited thereto.

Only one type of phosphorescent dopant material may be contained in the light emitting layer or two or more types may be contained. The content of phosphorescent dopant material is preferably 0.1 wt % to 30 wt %, and more preferably 1 wt % to 20 wt %, based on the weight of the host material.

Although there are no particular limitations on the phosphorescent dopant material, specific examples thereof are indicated below.

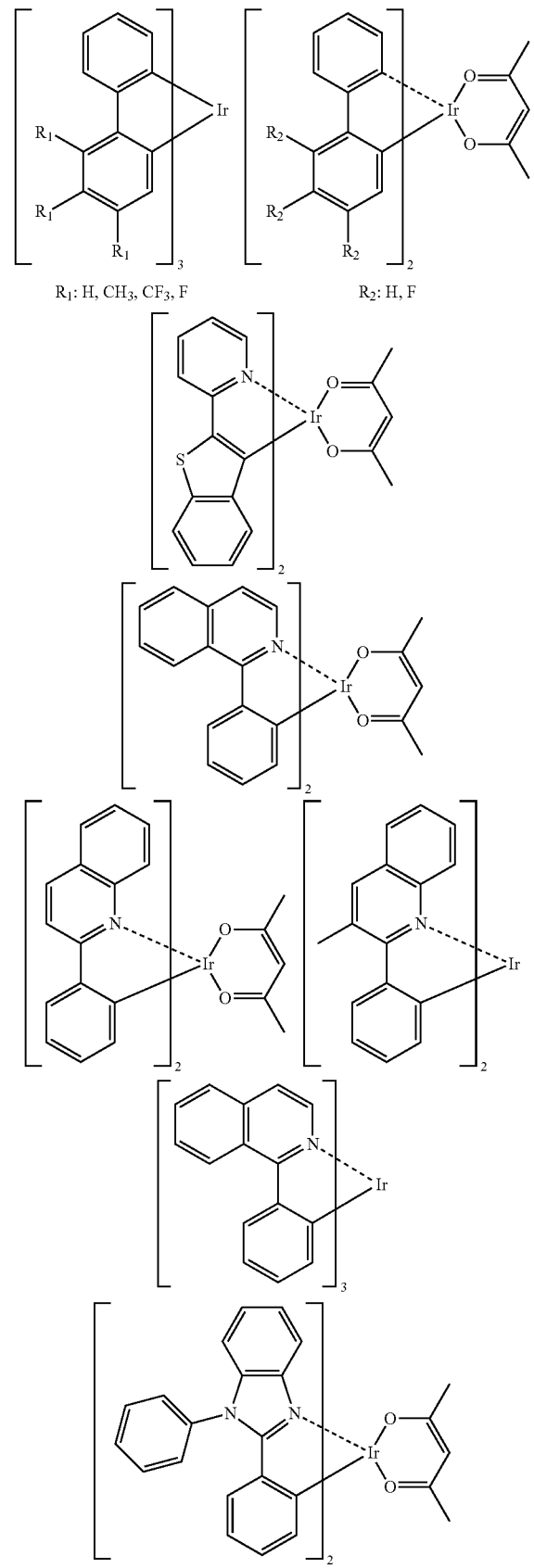

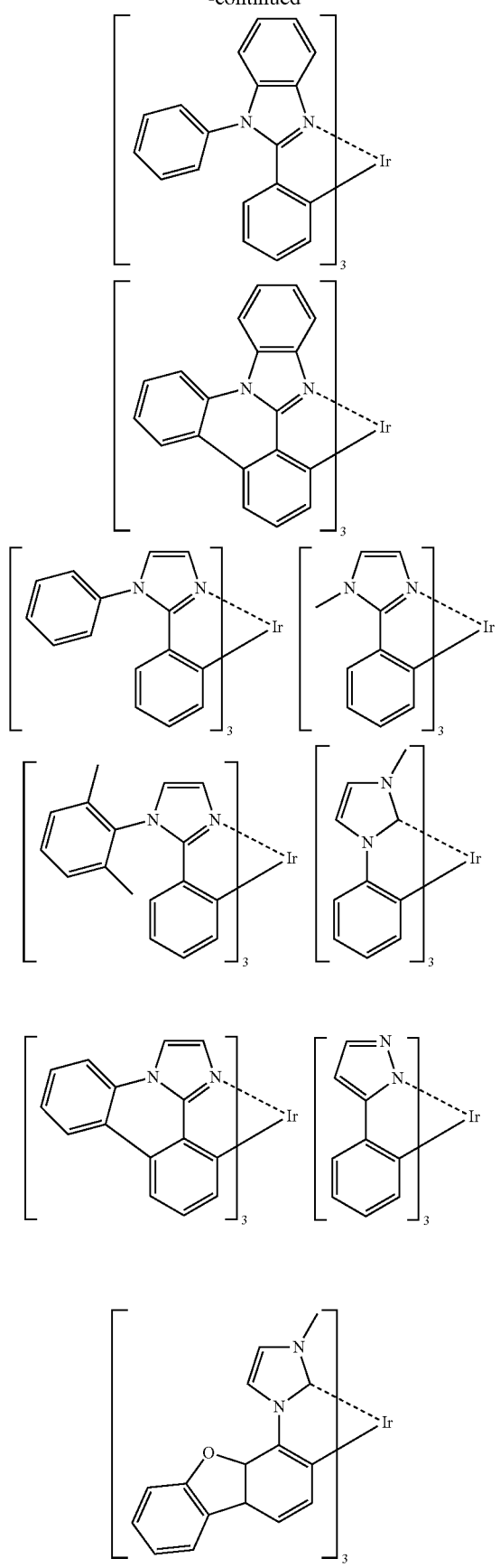
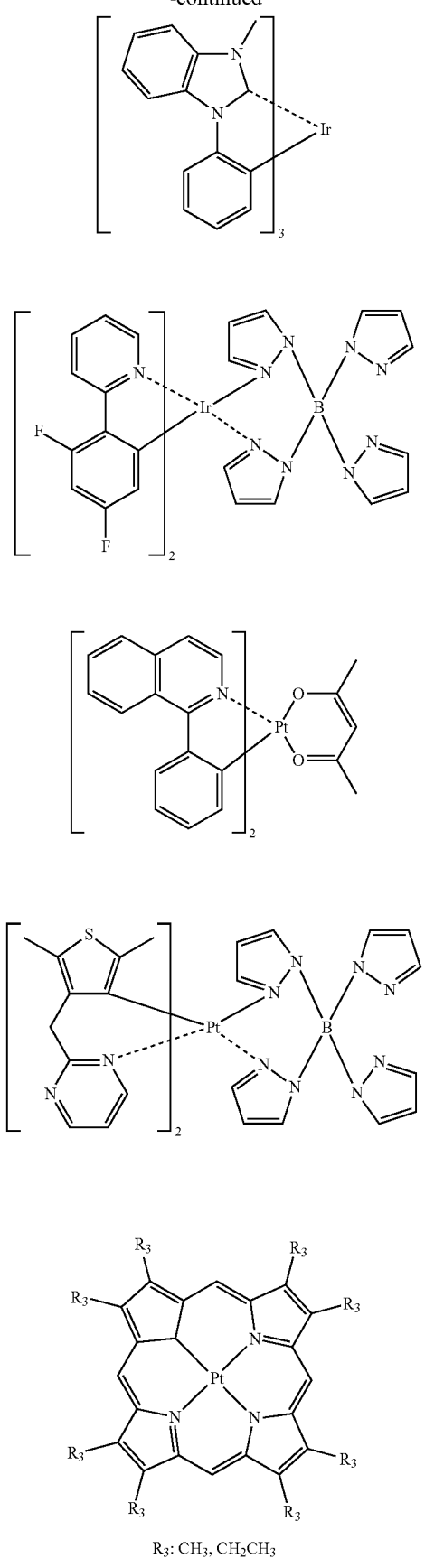

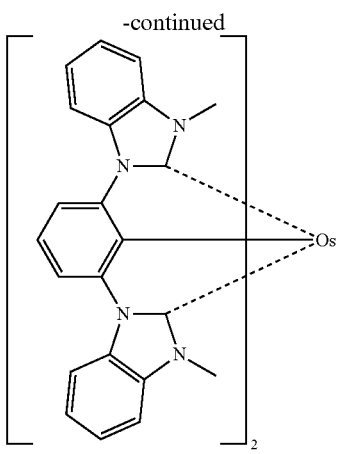

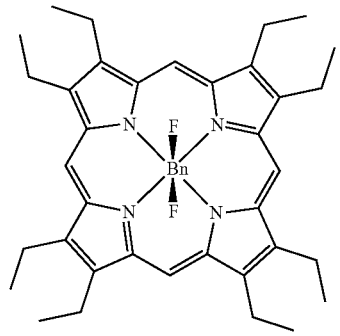

In the case of using a fluorescent dopant for the luminescent dopant material, there are no particular limitations on the fluorescent dopant and examples thereof include metal complexes of benzoxazole derivatives, benzothiazole derivatives, benzoimidazole derivatives, styrylbenzene derivatives, polyphenyl derivatives, diphenyl butadiene derivatives, tetraphenyl butadiene derivatives, naphthalimide derivatives, coumarin derivatives, condensed aromatic compounds, perinone compounds, oxadiazole derivatives, oxazine derivatives, aldazine derivatives, pyralizine derivatives, cyclopentadiene derivatives, bis-styrylanthracene derivatives, quinacridone derivatives, pyrrolopyridine derivatives, thiadiazolopyridine derivatives, styrylamine derivatives, diketopyrrolopyrrole derivatives, aromatic dimethylidine compounds and 8-quinolinol derivatives, various types of metal complexes represented by metal complexes of pyrromethene derivatives, rare earth complexes and transition metal complexes, polymer compounds such as polyolefin, polyphenylene or polyphenylenevinylene, and organic silane derivatives. Preferable examples include condensed aromatic derivatives, styryl derivatives, diketopyrrolopyrrole derivatives, oxazine derivatives, pyrromethene metal complexes, transition metal complexes and lanthanoid complexes, and more preferable examples include naphthalene, pyrene, chrysene, triphenylene, benzo[c]phenanthrene, benzo[a]anthracene, pentacene, perylene, fluoranthene, acenaphthofluoranthrene, dibenzo[a,j]anthracene, dibenzo[a,h]anthracene, benzo[a]naphthalene, hexacene, naphtho[2,1-f]isoquinoline, α-naphthaphenanthridine, phenanthroxazole, quinoline[6,5-f]quinoline and benzothiophanthrene. These may also have substituents in the form of an alkyl group, aryl group, aromatic heterocyclic group or diarylamino group.

Only one type of fluorescent dopant material may be contained in the light emitting layer or two or more types may be contained. The content of fluorescent dopant material is preferably 0.1% by weight to 20% by weight, and preferably 1% by weight to 10% by weight, based on the weight of the host material.

In the case of using a thermally activated delayed fluorescent dopant for the luminescent dopant material, there are no particular limitations on the thermally activated delayed fluorescent dopant, and examples thereof include metal complexes such as tin complexes or copper complexes, indolocarbazole complexes as described in WO 2011/070963, cyanobenzene complexes as described in Nature, 2012, 492, p. 234, and carbazole derivatives.

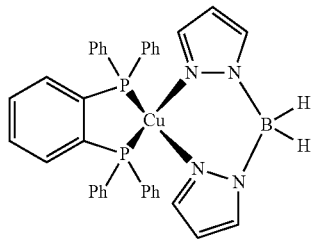

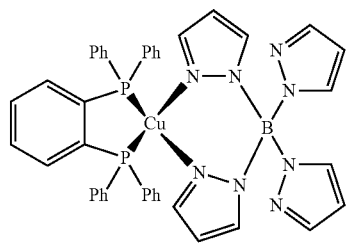

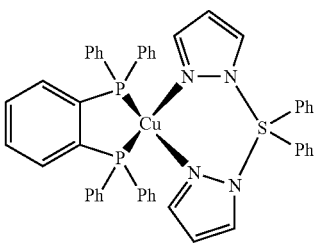

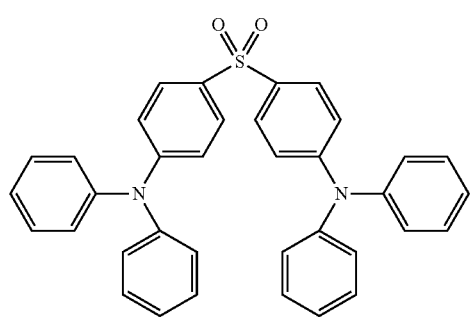

-continued
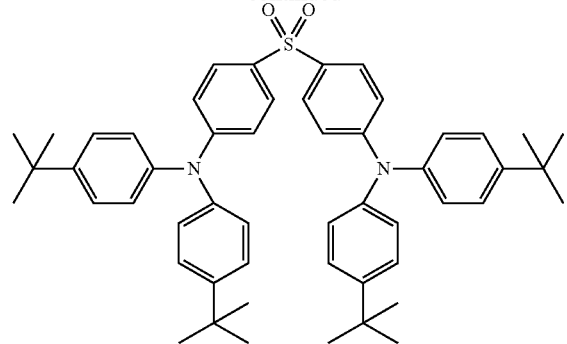
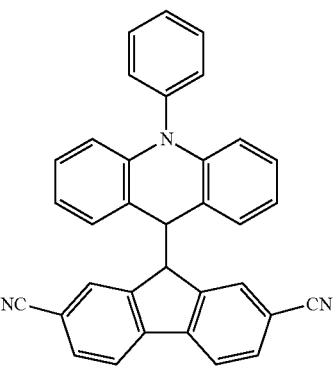
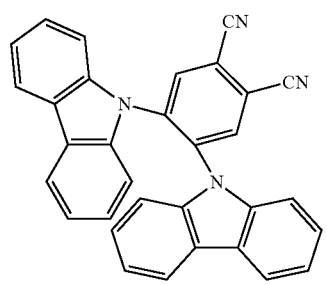
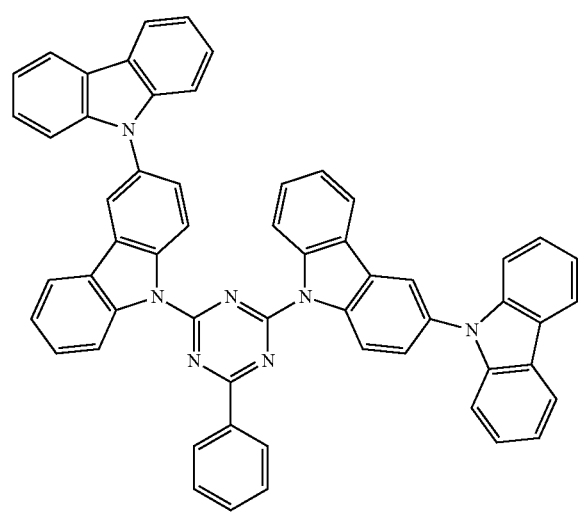
-continued
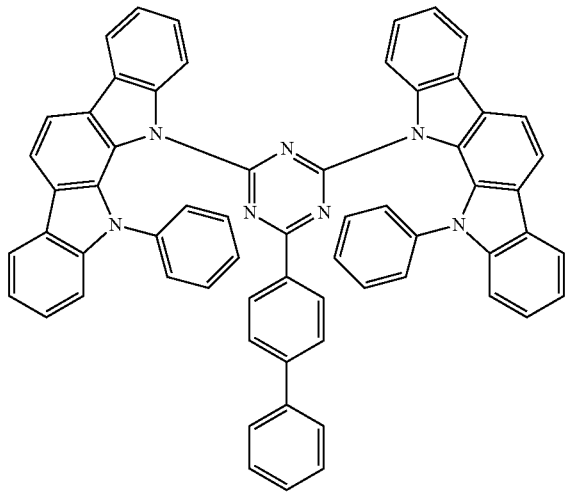
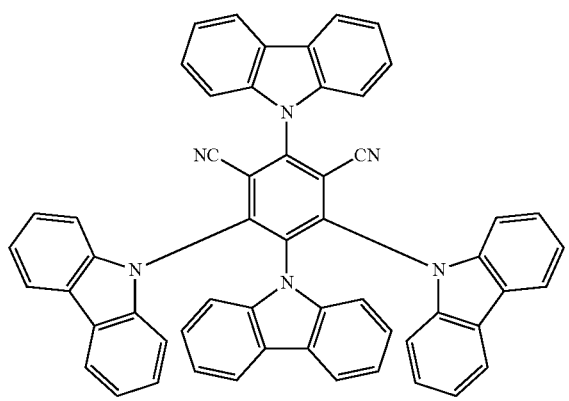

-continued

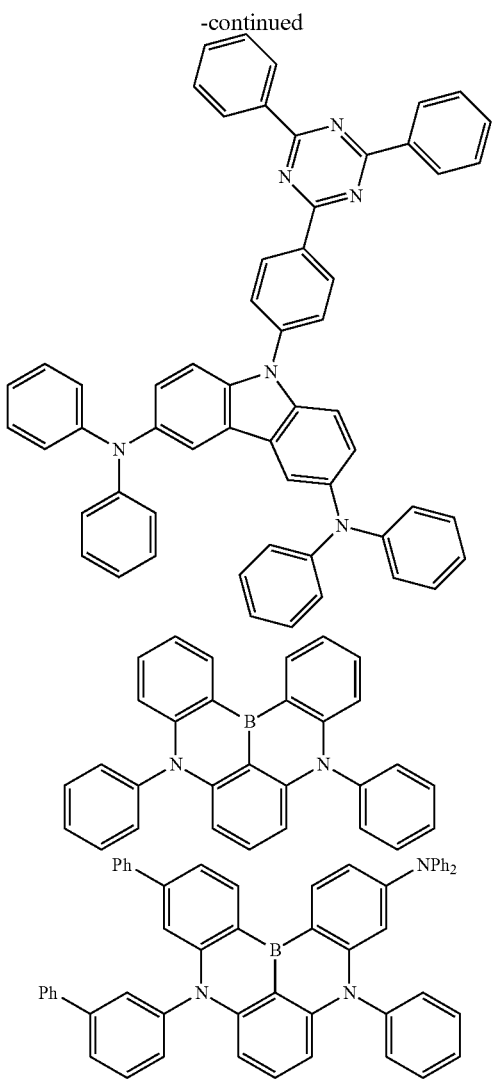

Only one type of thermally activated delayed fluorescent dopant may be contained in the light emitting layer or two or more types may be contained. In addition, a thermally activated delayed fluorescent dopant may be mixed with a phosphorescent dopant or fluorescent dopant. The content of thermally activated delayed fluorescent dopant is preferably 0.1% by weight to 50% by weight, and more preferably 1% by weight to 30% by weight, based on the weight of the host material.

Only one type of host material may be used or a plurality of types may be used in combination. There are no particular limitations on the host material and examples thereof that can be used include compounds having a condensed aromatic hydrocarbon ring, such as naphthalene, anthracene, phenanthrene, pyrene, chrysene, naphthacene, triphenylene, perylene, fluoranthene, fluorene or indene, and derivatives thereof, aromatic amine derivatives such as N,N'-dinaphthyl-N,N'-diphenyl-1,1'-diamine, metal complexes such as tris(8-quinolinato)ammonium (III), dibenzofuran derivatives, dibenzothiophene derivatives, carbazole derivatives, indolocarbazole derivatives and triazine derivatives. In the case of only using one type of host material and in the case of using a plurality of types of host materials, at least one type preferably uses an indolocarbazole derivative, and more preferably uses a compound represented by general formula (1).

—Injection Layers—

The injection layers refer to layers provided between the positive electrode and organic layer in order to lower the voltage at which the device is driven and improve emission luminance, include the hole injection layer and electron injection layer, and may be present between the anode and light emission layer or hole transport layer and between the cathode and the light emission layer or electron transport layer. Injection layers can be provided as necessary.

—Electron Blocking Layer—

The electron blocking layer refers to that having the function of a hole transport layer in the broad sense, and is able to improve the probability of electrons and holes recombining in the light emission layer by blocking electrons while transporting holes.

A known electron blocking layer material can be used for the material of the electron blocking layer or a material of the hole transport layer to be subsequently described can be used as necessary. The film thickness of the electron blocking layer is preferably 3 nm to 100 nm and more preferably 5 nm to 30 nm.

—Hole Transport Layer—

The hole transport layer is formed of a hole transport material that has the function of transporting holes, and a single hole transport layer or a plurality of hole transport layers can be provided.

The hole transport material has any of the abilities to inject holes or transport holes or block electrons, and may include an organic material or inorganic material. An arbitrary compound can be selected from among conventionally known compounds for use in the hole transport layer. Although examples of hole transport materials include porphyrin derivatives, arylamine derivatives, triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, anilino-based copolymers and electrically conductive polymer oligomers such as thiophene oligomers in particular, porphyrin derivatives, arylamine derivatives and styrylamine derivatives are used preferably, and arylamine compounds are used more preferably.

—Electron Transport Layer—

One type or two or more types of electron transport layers may be provided. In the case of providing two or more electron transport layers, the layer closest to the light emitting layer is referred to as the first electron transport layer and the layer farthest from the light emitting layer is referred to as the second electron transport layer. A third electron transport layer may be provided between the first electron transport layer and second electron transport layer.

In the case of a singlet electron transport layer, that layer contains a compound represented by the above-mentioned general formula (I) and an electron donor.

In the case of two or more electron transport layers, any one of the electron transport layers contains a compound represented by general formula (1) and an electron donor. Preferably the first electron transport layer contains a compound represented by general formula (I) and the second electron transport layer contains a compound represented by general formula (1) and an electron donor. In this case, the first electron transport layer does not contain an electron donor.

The following provides an explanation of the case of having a first electron transport layer and a second electron transport layer.

The first electron transport layer may be formed using a known electron transport material, may be formed using only a compound represented by general formula (1), or may be formed using a compound represented by general formula (1) in combination with a known electron transport material. However, the first electron transport layer preferably contains 50 wt % or more of a compound represented by general formula (1).

Known examples of electron transport materials include polycyclic aromatic derivatives such as naphthalene, anthracene, phenanthroline or triphenylene, tris(8-quinolinato)aluminum (III) derivatives, phosphine oxide derivatives, nitro-substituted fluorene derivatives, diphenylquinone derivatives, thiopyran dioxide derivatives, carbodimides, fluorenylidene methane derivatives, anthraquinodimethane and anthrone derivatives, bipyridine derivatives, quinoline derivatives, oxadiazole derivatives, benzoimidazole derivatives, benzothiazole derivatives, carbazole derivatives and indolocarbazole derivatives.

The second electron transport layer contains a compound represented by general formula (1) and an electron donor.

The content of electron donor in the second electron transport layer is preferably 5 wt % to 95 wt % and more preferably 25% by weight to 75% by weight. The content of a compound represented by general formula (1) is preferably 5% by weight to 90% by weight and more preferably 25% by weight to 75% by weight. The second electron transport layer can also contain other electron transport materials.

The compound represented by general formula (1) and electron donor can be vapor-deposited from respectively different deposition sources, or can be premixed prior to vapor deposition to forma premix to simultaneously deposit the compound represented by general formula (1) and the electron donor from a single deposition source. Although a known method such as mixed grinding can be employed for the premixing method, the materials are preferably mixed as completely as possible.

EXAMPLES

Although the following provides a more detailed explanation of the present invention through examples thereof, the present invention is not limited to these examples, but rather can be worked in various forms provided the gist thereof is not exceeded.

Example 1

Various thin films were laminated on a glass substrate having an anode, formed of ITO formed thereon at a film thickness of 110 nm, by vacuum deposition at a degree of vacuum of $4.0 \times 10^{-5}$ Pa. First, a hole injection layer in the form of HAT-CN was formed to a thickness of 25 nm on the ITO, after which a hole transport layer in the form of NPD was formed thereon to a thickness of 30 nm. Next, an electron blocking layer in the form of HT-1 was formed to a thickness of 10 nm. A first host in the form of Compound 6, a second host in the form of H1, and a luminescent dopant in the form of Ir(ppy)$_3$ were each co-deposited from different deposition sources to form a light emitting layer having a thickness of 40 nm. At this time, the materials were co-deposited under deposition conditions including an Ir (ppy)$_3$ concentration of 10% by weight and weight ratio of the first host to the second host of 40:60. Next, a first electron transport layer in the form of Compound 6 was formed to a thickness of 5 nm. Compound 6 and Liq were each co-deposited from different deposition sources to form a second electron transport layer to a thickness of 15 nm. At this time, the materials were co-deposited under deposition conditions including the weight ratio of Compound 6 to Liq being 50:50. Moreover, an electron injection layer in the form of Liq was additionally formed to a thickness of 1 nm. Finally, a cathode in the form of Al was formed on the electron injection layer to a thickness of 70 nm to produce an organic EL device.

Examples 2 to 7

Organic EL devices were produced under the same conditions as Example 1 with the exception of using any of Compounds 12, 16, 18, 23, 28 and 36 to form the second electron transport layer instead of Compound 6 used in Example 1.

Example 8

An organic EL device was produced under the same conditions as Example 1 with the exception of using Compound 47 to form the second electron transport layer instead of Compound 6 used in Example 1 and co-depositing under deposition conditions including a weight ratio of Compound 47 to Liq of 30:70.

Example 9

An organic EL device was produced under the same conditions as Example 1 with the exception of using Compound 55 to form the second electron transport layer instead of Compound 6 used in Example 1 and co-depositing under deposition conditions including a weight ratio of Compound 55 to Liq of 70:30.

Examples 10 to 12

Organic EL devices were produced under the same conditions as Example 1 with the exception of using Compound 10, 11 or 16 for the first electron transport layer instead of Compound 6 used in Example 1.

Example 13

A Premix E1 was prepared by weighing out Compound 17 (0.50 g) and Liq (0.50 g) and mixing while crushing with a mortar and pestle.

Various thin films were laminated on a glass substrate having an anode, formed of ITO formed thereon at a film thickness of 110 nm, by vacuum deposition at a degree of vacuum of $4.0 \times 10^{-5}$ Pa. First, a hole injection layer in the form of HAT-CN was formed to a thickness of 25 nm on the ITO, after which a hole transport layer in the form of NPD was formed thereon to a thickness of 30 nm. Next, an electron blocking layer in the form of HT-1 was formed to a thickness of 10 nm. A first host in the form of Compound 6, a second host in the form of H1, and a luminescent dopant in the form of Ir(ppy)$_3$ were each co-deposited from different deposition sources to form a light emitting layer having a thickness of 40 nm. At this time, the materials were co-deposited under deposition conditions including an Ir(ppy)$_3$ concentration of 10 wt % and weight ratio of the first host to the second host of 40:60. Next, a first electron transport layer in the form of Compound 6 was formed to a thickness of 5 nm. A second electron transport layer in the form of Premix E1 was formed to a thickness of 15 nm followed by additionally forming an electron injection layer in the form of Liq to a thickness of 1 nm. Finally, a cathode in the form of Al was formed on the electron injection layer to a thickness of 70 nm to produce an organic EL device.

Comparative Example 1

An organic EL device was produced under the same conditions as Example 1 with the exception of using ET-1 to form the second electron transport layer instead of Compound 6 used in Example 1.

Comparative Example 2

Various thin films were laminated on a glass substrate having an anode, formed of ITO formed thereon at a film thickness of 110 nm, by vacuum deposition at a degree of vacuum of $4.0 \times 10^{-5}$ Pa. First, a hole injection layer in the form of HAT-CN was formed to a thickness of 25 nm on the ITO, after which a hole transport layer in the form of NPD was formed thereon to a thickness of 30 nm. Next, an electron blocking layer in the form of HT-1 was formed to a thickness of 10 nm. A first host in the form of Compound 6, a second host in the form of H1, and a luminescent dopant in the form of Ir(ppy)$_3$ were each co-deposited from different deposition sources to form a light emitting layer having a thickness of 40 nm. At this time, the materials were co-deposited under deposition conditions including an Ir(ppy)$_3$ concentration of 5 wt % and weight ratio of the first host to the second host of 40:60. Next, a first electron transport layer in the form of Compound 6 was formed to a thickness of 20 nm. An electron injection layer in the form of Liq was additionally formed to a thickness of 1 nm. Finally, a cathode in the form of Al was formed on the electron injection layer to a thickness of 70 nm to produce an organic EL device.

The compounds used in the examples are shown below.

[C11]

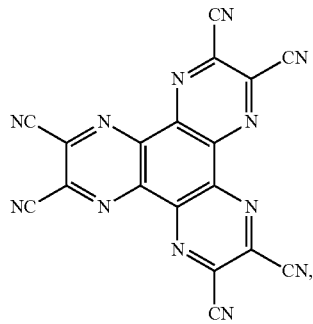

HAT-CN

-continued

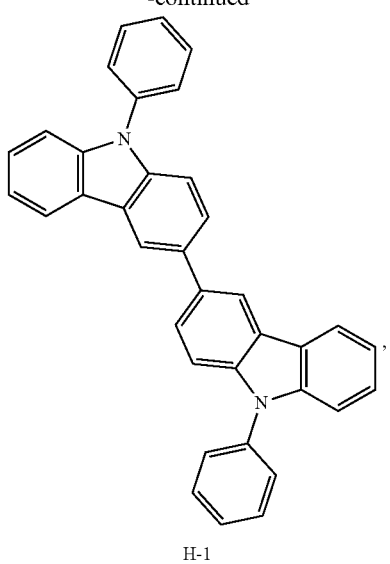

H-1

Compounds used to form the first electron transport layer, compounds used to form the second electron transport layer and the electron donors are shown in Table 1. Percent indicates percent by weight (wt %).

TABLE 1

|  | First Electron Transport Layer | Second Electron Transport Layer |
| --- | --- | --- |
| Example 1 | Compound 6 | Compound 6 (50%) + Liq (50%) |
| Example 2 | Compound 6 | Compound 12 (50%) + Liq (50%) |
| Example 3 | Compound 6 | Compound 16 (50%) + Liq (50%) |
| Example 4 | Compound 6 | Compound 18 (50%) + Liq (50%) |
| Example 5 | Compound 6 | Compound 23 (50%) + Liq (50%) |
| Example 6 | Compound 6 | Compound 28 (50%) + Liq (50%) |
| Example 7 | Compound 6 | Compound 36 (50%) + Liq (50%) |
| Example 8 | Compound 6 | Compound 47 (50%) + Liq (70%) |
| Example 9 | Compound 6 | Compound 55 (50%) + Liq (30%) |
| Example 10 | Compound 10 | Compound 6 (50%) + Liq (50%) |
| Example 11 | Compound 11 | Compound 6 (50%) + Liq (50%) |
| Example 12 | Compound 16 | Compound 6 (50%) + Liq (50%) |
| Example 13 | Compound 6 | Compound 17 (50%) + Liq (50%) |
| Comparative Example 1 | Compound 6 | ET-1 (50%) + Liq (50%) |
| Comparative Example 2 |  | Compound 6 |

When the organic EL devices produced in Examples 1 to 13 and Comparative Examples 1 and 2 were connected to an external power supply and a voltage was applied thereto, emission spectra were observed at a maximum wavelength of 535 nm, and emission of light was determined to be obtained from Ir(ppy)$_3$.

Luminance, drive voltage, luminous efficiency and service life characteristics of the produced organic EL devices are shown in Table 2. In the table, luminance, drive voltage and luminous efficiency indicate values obtained when driving the devices at a current of 10 mA/cm$^2$ and represent the initial values. In the table, LT95 indicates the amount of time required for luminance to attenuate to 95% of initial luminance when driven at a current of 20 mA/cm$^2$.

TABLE 2

|  | Luminance (cd/m$^2$) | Voltage (V) | Luminous efficiency (lm/W) | LT95 (h) |
| --- | --- | --- | --- | --- |
| Example 1 | 4861 | 4.3 | 35.8 | 93 |
| Example 2 | 4822 | 4.4 | 34.4 | 90 |
| Example 3 | 4899 | 4.0 | 38.5 | 101 |
| Example 4 | 4954 | 4.4 | 35.4 | 105 |
| Example 5 | 4788 | 4.3 | 35.0 | 89 |
| Example 6 | 4726 | 4.5 | 33.0 | 85 |
| Example 7 | 4877 | 4.6 | 33.3 | 81 |
| Example 8 | 4927 | 4.3 | 36.0 | 108 |
| Example 9 | 4819 | 4.4 | 34.4 | 93 |
| Example 10 | 4815 | 4.2 | 36.0 | 96 |
| Example 11 | 4799 | 4.3 | 35.0 | 90 |
| Example 12 | 4746 | 4.1 | 36.3 | 97 |
| Example 13 | 4833 | 4.2 | 36.1 | 95 |
| Comparative Example 1 | 4589 | 4.6 | 31.3 | 71 |
| Comparative Example 2 | 3982 | 5.7 | 21.9 | 5 |

Based on the results shown in Table 2, when a compound represented by general formula (1) and an electron donor were mixed and used in the electron transport layers, luminous efficiency and service life characteristics were determined to improve considerably.

INDUSTRIAL APPLICABILITY

The organic EL device of the present invention demonstrates high luminous efficiency when driven at low voltage as well as a long service life, and in addition to being able to be used in the displays of portable devices, can also be used in the organic EL displays of applications such as televisions as well as for organic EL lighting.

REFERENCE SIGNS LIST

1 Substrate
2 Anode
3 Hole injection layer
4 Hole transport layer
5 Light emitting layer
6 First electron transport layer
7 Second electron transport layer
8 Cathode

The invention claimed is:

1. An organic electroluminescent device containing one or more light emitting layers and one or more electron transport layers between opposing anode and cathode, wherein at least one of the electron transport layers contains a compound represented by general formula (1) below and an electron donor, wherein, in a case of two or more electron transport layers, a first electron transport layer contains the compound represented by general formula (1) without the electron donor, and a second transport layer contains the compound represented by general formula (1) and the electron donor:

[C1]

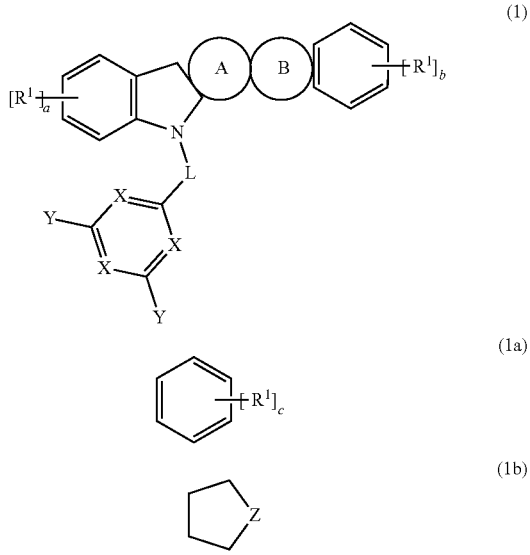

(1)

(1a)

(1b)

wherein, ring A represents an aromatic hydrocarbon ring represented by formula (1a), ring B represents a heterocyclic ring represented by formula (1b), and ring A and ring B are condensed with a ring adjacent to ring A and ring B at arbitrary locations, L represents a single bond or aromatic hydrocarbon group having 6 to 12 carbon atoms, X represents N or C—Ar¹ and at least one of X represents N, Y and Ar¹ respectively and independently represent a hydrogen atom, substituted or unsubstituted aromatic hydrocarbon group having 6 to 18 carbon atoms, substituted or unsubstituted aromatic heterocyclic group having 3 to 18 carbon atoms, or a linked aromatic group obtained by linking 2 to 5 of these aromatic rings, R¹ independently represents an aliphatic hydrocarbon group having 1 to 10 carbon atoms, a substituted or unsubstituted aromatic hydrocarbon group having 6 to 10 carbon atoms, or a substituted or unsubstituted aromatic heterocyclic group having 3 to 12 carbon atoms, and a, b and c respectively and independently represent an integer of 0 to 3, Z represents N—Ar², C(R²)₂, O or S, wherein Ar² represents a substituted or unsubstituted aromatic hydrocarbon group having 6 to 18 carbon atoms, a substituted or unsubstituted aromatic heterocyclic group having 3 to 18 carbon atoms, or a linked aromatic group obtained by linking 2 to 5 of these aromatic rings, and R² independently represents a hydrogen atom, aliphatic hydrocarbon group having 1 to 10 carbon atoms, substituted or unsubstituted aromatic hydrocarbon group having 6 to 10 carbon atoms, or substituted or unsubstituted aromatic heterocyclic group having 3 to 12 carbon atoms.

2. The organic electroluminescent device according to claim 1, wherein the heterocyclic ring represented by formula (1b) is a heterocyclic ring represented by formula (1d):

[C2]

(1d)

where, Ar¹ has the same meaning as in general formula (1).

3. The organic electroluminescent device according to claim 1, wherein L in general formula (1) represents a single bond.

4. The organic electroluminescent device according to claim 1, wherein the electron transport layer is formed of two layers, which are the first electron transport layer being adjacent to the light emitting layer and the second electron transport layer being adjacent to the first layer.

5. The organic electroluminescent device according to claim 1, wherein the electron donor is an alkaline metal compound or alkaline metal complex.

6. The organic electroluminescent device according to claim 5, wherein the electron donor is quinolilato-lithium.

7. A method of manufacturing the organic electroluminescent device according to claim 1, comprising:
depositing a premix of a compound represented by general formula (1) and electron donor to obtain the electron transport layer.

8. An organic electroluminescent device containing one or more light emitting layers and one or more electron transport layers between opposing anode and cathode, wherein at least one of the electron transport layers contains a compound represented by general formula (1) below and an electron donor:

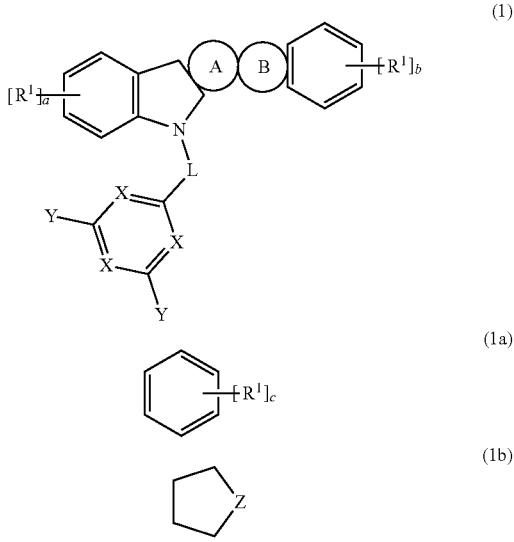

(1)

(1a)

(1b)

wherein, ring A represents an aromatic hydrocarbon ring represented by formula (1a), ring B represents a heterocyclic ring represented by formula (1b), and ring A and ring B are condensed with a ring adjacent to ring A and ring B at arbitrary locations, L represents a single bond or aromatic hydrocarbon group having 6 to 12 carbon atoms, X represents N or C—$Ar^1$ and at least one of X represents N, Y and $Ar^1$ respectively and independently represent a hydrogen atom, substituted or unsubstituted aromatic hydrocarbon group having 6 to 18 carbon atoms, substituted or unsubstituted aromatic heterocyclic group having 3 to 18 carbon atoms, or a linked aromatic group obtained by linking 2 to 5 of these aromatic rings, $R^1$ independently represents an aliphatic hydrocarbon group having 1 to 10 carbon atoms, a substituted or unsubstituted aromatic hydrocarbon group having 6 to 10 carbon atoms, or a substituted or unsubstituted aromatic heterocyclic group having 3 to 12 carbon atoms, and a, b and c respectively and independently represent an integer of 0 to 3, Z represents N—$Ar^2$, $C(R^2)_2$, O or S, wherein $Ar^2$ represents a substituted or unsubstituted aromatic hydrocarbon group having 6 to 18 carbon atoms, a substituted or unsubstituted aromatic heterocyclic group having 3 to 18 carbon atoms, or a linked aromatic group obtained by linking 2 to 5 of these aromatic rings, and $R^2$ independently represents a hydrogen atom, aliphatic hydrocarbon group having 1 to 10 carbon atoms, substituted or unsubstituted aromatic hydrocarbon group having 6 to 10 carbon atoms, or substituted or unsubstituted aromatic heterocyclic group having 3 to 12 carbon atoms, wherein the light emitting layer contains a host material and a luminescent material, the light emitting layer containing as the host material a compound represented by general formula (1).

* * * * *